(12) United States Patent
Hancock et al.

(10) Patent No.: US 12,059,203 B2
(45) Date of Patent: Aug. 13, 2024

(54) ELECTROSURGICAL PROBE FOR DELIVERING MICROWAVE ENERGY

(71) Applicant: CREO MEDICAL LIMITED, Chepstow (GB)

(72) Inventors: Christopher Paul Hancock, Bath (GB); Malcolm White, Chepstow (GB); Patrick Burn, Chepstow (GB); Pallav Shah, London (GB); Philip Hales, Newport Gwent (GB)

(73) Assignee: CREO MEDICAL LIMITED, Chepstow (GB)

( * ) Notice: Subject to any disclaimer, the term of this patent is extended or adjusted under 35 U.S.C. 154(b) by 691 days.

(21) Appl. No.: 16/061,640

(22) PCT Filed: Dec. 16, 2016

(86) PCT No.: PCT/EP2016/081584
§ 371 (c)(1),
(2) Date: Jun. 12, 2018

(87) PCT Pub. No.: WO2017/103209
PCT Pub. Date: Jun. 22, 2017

(65) Prior Publication Data
US 2019/0069951 A1 Mar. 7, 2019

(30) Foreign Application Priority Data
Dec. 17, 2015 (GB) ...................... 1522312

(51) Int. Cl.
*A61B 18/00* (2006.01)
*A61B 18/14* (2006.01)
*A61B 18/18* (2006.01)

(52) U.S. Cl.
CPC ...... *A61B 18/1815* (2013.01); *A61B 18/1492* (2013.01); *A61B 2018/00071* (2013.01);
(Continued)

(58) Field of Classification Search
CPC ............ A61B 18/1815; A61B 18/1492; A61B 2018/00071; A61B 2018/00107;
(Continued)

(56) References Cited

U.S. PATENT DOCUMENTS

| 5,057,106 A | 10/1991 | Kasevich et al. |
| 6,230,060 B1 | 5/2001 | Mawhinney |

(Continued)

FOREIGN PATENT DOCUMENTS

| EP | 2386261 A2 | 11/2011 |
| EP | 2399646 A1 | 12/2011 |

(Continued)

OTHER PUBLICATIONS

British Search Report issued in British Patent Application No. GB1522312.6, mailed Aug. 30, 2016.
(Continued)

*Primary Examiner* — Sean W Collins
*Assistant Examiner* — Rachel A. Vierra
(74) *Attorney, Agent, or Firm* — ArentFox Schiff LLP

(57) ABSTRACT

An electrosurgical instrument for use in minimally invasive surgical techniques that provides a small scale localized microwave field capable of precisely ablating tissue, e.g. in the lungs, through suitable selection of geometry and material for a radiating distal tip thereof. The instrument may be used with a bronchoscope having a power delivery structure formed within the instrument cord thereof. A vision system may be incorporated into the energy delivery structure. The instrument comprise a coaxial cable for conveying microwave energy to a radiating tip portion that comprises a dielectric tip and a distal conductive portion that extends longitudinally therein. The dielectric tip has a dielectric constant greater than a dielectric material within the coaxial cable. The distal end of the device is designed to facilitate (Continued)

efficient microwave energy delivery into lung tumour tissue to achieve a localized volume of ablation.

28 Claims, 13 Drawing Sheets

(52) U.S. Cl.
CPC ............... *A61B 2018/00107* (2013.01); *A61B 2018/00541* (2013.01); *A61B 2018/00577* (2013.01); *A61B 2018/00702* (2013.01); *A61B 2018/00791* (2013.01); *A61B 2018/00821* (2013.01); *A61B 2018/00982* (2013.01); *A61B 2018/183* (2013.01); *A61B 2018/1861* (2013.01)

(58) Field of Classification Search
CPC ........... A61B 2018/00541; A61B 2018/00577; A61B 2018/00702; A61B 2018/00791; A61B 2018/00821; A61B 2018/00982; A61B 2018/183; A61B 2018/1861
See application file for complete search history.

(56) References Cited

U.S. PATENT DOCUMENTS

| | | |
|---|---|---|
| 6,287,302 B1 | 9/2001 | Berube |
| 2003/0100894 A1* | 5/2003 | Mahon ............... A61B 18/1815 606/41 |
| 2008/0221650 A1* | 9/2008 | Turner ............... A61B 18/1815 607/102 |
| 2009/0299360 A1* | 12/2009 | Ormsby ............. A61B 18/1492 606/33 |
| 2010/0030207 A1 | 2/2010 | Hancock |
| 2010/0228244 A1* | 9/2010 | Hancock ............ A61B 18/1815 606/33 |
| 2011/0034917 A1 | 2/2011 | Brannan |
| 2011/0077635 A1* | 3/2011 | Bonn ....................... H01Q 9/16 343/906 |
| 2011/0190630 A1 | 8/2011 | Kim et al. |
| 2013/0072924 A1* | 3/2013 | Burgener ............... H01Q 11/08 29/600 |
| 2013/0267943 A1* | 10/2013 | Hancock ................ H05B 6/806 606/33 |
| 2014/0276739 A1* | 9/2014 | Brannan ................ A61B 34/25 606/33 |
| 2014/0290830 A1 | 10/2014 | Brannan |
| 2015/0112190 A1 | 4/2015 | Hancock |

FOREIGN PATENT DOCUMENTS

| | | |
|---|---|---|
| GB | 2532345 A | 10/2015 |
| JP | 59-17361 A | 1/1984 |
| JP | 2008-142467 A | 6/2008 |
| JP | 2013-523346 A | 6/2013 |
| JP | 2015-163232 A | 9/2015 |
| WO | WO 2011/127216 A2 | 10/2011 |

OTHER PUBLICATIONS

British Search Report issued in British Patent Application No. GB1522312.6, mailed May 11, 2016.
International Preliminary Report on Patentability issued in PCT Application No. PCT/EP2016/081584, mailed on Feb. 15, 2018.
International Search Report and Written Opinion issued in PCT Application No. PCT/EP2016/081584, mailed Apr. 12, 2017.
Communication from the Japanese Patent Office in counterpart application No. 2018-531513, dated Dec. 15, 2020.

* cited by examiner

ELECTROSURGICAL PROBE FOR DELIVERING MICROWAVE ENERGY

CROSS-REFERENCE TO RELATED APPLICATIONS

This application is a National Phase entry of International Application No. PCT/EP2016/081584, filed Dec. 16, 2016, which claims priority to British Patent Application No. 1522312.6, filed Dec. 17, 2015. The disclosures of the priority applications are incorporated in their entirety herein by reference.

FIELD OF THE INVENTION

The invention relates to an electrosurgical probe for delivering microwave energy to biological tissue in order to ablate the target tissue. In particular, the probe can be used in the lungs or in the uterus, e.g. to ablate tumours, lesions or fibroids and to treat asthma. The probe may be inserted through a channel of a bronchoscope or catheter, or may be used in laparoscopic surgery or open surgery.

BACKGROUND TO THE INVENTION

It is inherently difficult to gain access to lung tumours due to the small dimensions of the bronchial tree, especially towards the peripheral regions where small nodules are likely to develop. This has resulted in many treatment options being employed such as chemotherapy (targeted medicine, anti-cancer drugs (chemotherapeutic agents)), radiotherapy (delivery of ionizing radiation), surgery (invasive and minimally invasive) and RF/microwave ablation. Surgical procedures involve pneumonectomy (removal of one lung), lobectomy (removal of a lobe), sleeve lobectomy (resection of a lobe along with part of the bronchus that attaches to it), wedge resection (removal of a wedge shaped portion of lung) and segmentectomy/segment resection (resection of a specific lung segment).

It is known to use microwave emitting probes to treat various conditions in the lungs and other body tissues. For example, in the lungs, microwave radiation can be used to treat asthma and ablate tumours or lesions.

Existing microwave ablation devices on the market are designed to be inserted percutaneously. However, such devices are difficult to locate percutaneously into a moving lung, which can lead to complications such as pneumothorax and haemothorax (air and blood within the pleural cavity respectively).

Using a probe to deliver the energy to target tissue is preferable because the radiating portion can be positioned close to the target site and so a high proportion of power can be transmitted to the target site and a lower proportion is lost to the surrounding healthy tissue. This reduces side effects of treatment as well as increasing efficiency.

Efficient lung cancer treatment through minimally invasive procedures is desirable to reduce the mortality rate of lung cancer patients and to reduce the intraoperative and postoperative complication rate. Probes can be inserted into tissue via laparoscopic surgery, open surgery or via channels in the body such as airways. The least invasive method is the use of channels in the body and this reduces strain put on a patient by the procedure. Catheters or bronchoscopes can be used to help to guide the instrument to the target site and some examples of the mechanisms used are given in US2009/306644.

In US2014/046174, a microwave ablation catheter is disclosed with a radiating section that is delivered to the target site by a bronchoscope through the airways of a patient.

Various designs of radiating portions can be used, such as a coaxial cable with a radiating portion on the distal end as in US2014/046174 and the energy delivery device of US2013/324995.

SUMMARY OF THE INVENTION

At its most general, one aspect of the invention provides an electrosurgical instrument for use in minimally invasive surgical techniques that provides, at a very small scale, a localized microwave field capable of precisely ablating tissue in the lungs. This is done through suitable selection of geometry and material for a radiating distal tip thereof. As explained in more detail below, another aspect of the invention integrate a power delivery structure within the instrument cord of a bronchoscope. Both aspects of the invention can be used in combination with each other and/or in conjunction with a steering control, temperature sensing and vision systems, to provide a practitioner with a rich source of feedback information during treatment.

According to one aspect of the invention, there is provided an electrosurgical instrument for delivering microwave energy into lung tissue, the electrosurgical instrument comprising: a coaxial cable for conveying microwave energy, the coaxial cable having an inner conductor, an outer conductor, and a first dielectric material separating the inner conductor and outer conductor; and a radiating tip portion disposed at a distal end of the coaxial cable to receive the microwave energy from the coaxial cable, wherein the radiating tip portion comprises: a dielectric tip formed from a second dielectric material that is different from the first dielectric material, and a distal conductive portion of the inner conductor, which extends longitudinally into the dielectric tip, and wherein the second dielectric material has a dielectric constant greater than the first dielectric material, whereby the radiating tip portion is arranged to radiate a localized microwave field for tissue ablation. The instrument is thus a coaxial-based device with a dielectric constant load at its distal end. The distal end of the device is designed to facilitate efficient microwave energy delivery into lung tumour tissue to achieve a localized volume of ablation. The resulting localized, thermally induced tissue damage (ablation zone) occurs as a result of dielectric heating. Other modes of energy delivery may be used. For example, the instrument may comprise conductive material arranged on an outer surface of the dielectric tip to form a microstrip of coplanar transmission line for delivering the microwave energy into biological tissue.

The instrument may also be configured to deliver radiofrequency (RF) energy.

The effect of the dielectric tip is to reduce the wavelength of the microwave energy, which allows better impedance matching and control of the resultant ablation profile based on small geometry constraints. For example, the outer diameter of the coaxial cable and radiating tip portion may be equal to or less than 1.9 mm, preferably equal to or less than 1.5 mm. This size enables the instrument to fit down and be manipulated by commercially available bronchoscope instrument channels. As explained below, the instrument may also include its own steering mechanism, which can allow it to be manoeuvred when it extends out from the end of the bronchoscope instrument channel.

In order to maintain flexibility of the device, the axial length of the dielectric tip is equal to or less than 3 mm, preferably equal to or less than 2 mm. This enables the second dielectric material to be relatively rigid without adversely affecting the flexibility of the instrument, especially at its distal end.

The microwave energy may be a single stable frequency, e.g. 5.8 GHz. The dielectric constant of the second dielectric material may be selected based on the frequency of the microwave energy such that the axial length of the dielectric tip corresponds to a non-negligible fraction of a wavelength of the microwave energy when propagating in the dielectric tip. Herein, a non-negligible fraction may be equal to or greater than 0.05, preferably more than 0.06. This can ensure that the second dielectric material provides a suitable wavelength-shortening effect. In one embodiment, the dielectric constant of the second dielectric material is equal to or greater than 80. For example, titanium dioxide may be used as the second dielectric material. PFTE or any other dielectric that is low loss at the frequency of the microwave energy may be used for the first dielectric material.

The radiating tip portion may be arranged to act as a quarter wave impedance transformer to match an input impedance to a tissue load impedance. In other words, the geometry of the radiating tip portion is selected so that the effects of the impedance mismatch are invisible when looking into the transmission line prior to the impedance transformer.

The radiating tip portion may further comprise an intermediate dielectric element surrounding a proximal part of the distal conductive portion and separating the first dielectric material from the dielectric tip, the intermediate dielectric element being formed from a third dielectric material that is different from the second dielectric material. The third dielectric material may be the same as or different from the first dielectric material. The geometry of the intermediate dielectric element can be selected, e.g. using simulations or the like to facilitate the impedance matching function discussed above.

An embodiment of the instrument may include a handle at the proximal end of the coaxial cable, e.g. to provide an interface to a suitable electrosurgical generator, and a closed ended catheter/sheath for conveying the coaxial cable and radiating tip portion.

The localized microwave field may be substantially spherical, e.g. around the radiating tip portion. The shortening of the wavelength of the microwave energy in the dielectric tip may prevent the microwave field from extending or elongating proximally, e.g. back down the length of the coaxial cable. One advantage of a spherical field shape is that it is rotation invariant, so the orientation of the instrument in the instrument channel does not need to be controlled.

However, in some circumstances an equal field on all sides of the radiating tip portion may not be wanted. Thus, the radiating tip portion may include a field shaping element arranged to direct the microwave field to one side of the radiating tip portion. The field shaping elements may include a choke comprising layers of dielectric and conductive material.

The field shaping element may be a conductive finger extending longitudinally along a side of an outer surface of the dielectric tip opposite to the side from which the microwave field is directed, the conductive finger being electrically connected to the outer conductor of the coaxial cable. The conductive finger thus acts as a reflector for the field to ensure that a majority of the microwave energy is emitted from one side of the radiating tip portion. The conductive finger preferably extends over a narrow circumferential portion of the dielectric tip. The narrower the circumferential dimension of the conductive finger, the better the impedance matching function.

The conductive finger preferably extends beyond the distal conductive portion. For example, the radiating tip portion may include a dielectric cap disposed distally to the dielectric tip and distal conductive portion, the conductive finger extending along an outer surface of the dielectric cap, whereby the conductive finger extends further from the coaxial cable than the distal conductive portion. This configuration also improves the impedance matching function. The dielectric cap is formed from a fourth dielectric material that is not the same as the second dielectric material. The fourth dielectric material is preferably a material that exhibits low loss for the microwave energy, and may be the same as the first dielectric material. Thus, the first dielectric material (i.e. the dielectric in the coaxial cable) may be the same as the third dielectric material (which acts as an isolating barrier for the outer conductor at the end of the coaxial cable) and the fourth dielectric material (which can form a distal tip of the device. All of these elements may be formed from PTFE, for example. The second dielectric material can be sandwiched between the third and fourth dielectric materials and has a higher dielectric constant. The second dielectric material can be made from titanium dioxide, for example.

The conductive finger may be an extension of the outer conductor of the coaxial cable. It may therefore be fixed on the dielectric tip. In this example, the instrument may be need to be rotatable in the instrument channel in order to control the position of the radiated microwave field.

However, in another embodiment, the conductive finger may be a distal part of a conductive sleeve mounted on and electrically connected to the outer conductor of the coaxial cable, wherein the conductive sleeve is rotatable relative the dielectric tip to adjust the circumferential position of the conductive finger. In this arrangement, the whole instrument does not need to be rotatable in the instrument channel. Only the conductive sleeve needs to be controlled. The orientation of the conductive sleeve may be controlled by a pair of guide wires or the like.

The conductive sleeve may be used to provide other types of field shaping element. For example, the field shaping element may be a conductive sleeve formed over the dielectric tip, the conductive sleeve having a radiating slot formed therein on the side from which the microwave field is directed. The conductive sleeve may be rotatable relative the dielectric tip to adjust the circumferential position of the radiating slot.

The conductive sleeve does not need to rotate. For example, the conductive sleeve may have a plurality of radially offset radiating slots around the outer surface of the dielectric tip, and the radiating top portion may comprise an actuator operable to selectively expose only one of the plurality of radiating slots. In an embodiment, the conductive sleeve may have a pair of radiating slots on opposite sides of the dielectric tip. The actuator may comprise a longitudinally slidable sleeve having radially offset (e.g. diametrically opposed) cut outs formed therein, wherein the actuator is movable between a first position in which a first cut out exposes a first one of the pair of radiating slots and a second position in which a second cut out exposes a second one of the pair of radiating slots. The relative positions of the cut outs and radiating slots is chosen to prevent both radiating slots from being exposed at the same time. For example the cut outs may be offset from one another in a longitudinal direction. In this example, the pair of radiating slots may be laterally aligned or offset by a different amount in order to avoid simultaneous exposure. In an embodiment, the actuator may be movable to a third position in which both slots are exposed, e.g. to enable a spherical field to be emitted.

The field shaping element may include a patch antenna formed on the dielectric tip. Alternatively, the field shaping element may comprise a leaky slotted line, i.e. a radiating element formed by providing a plurality of slots in the ground plane of a coaxial transmission line.

An outer sheath may be formed over the radiating tip portion, e.g. to provide biocompatibility and/or protect the instrument. The dielectric tip may have a geometry that assists manipulation of the instrument within the lung. For example, the distal end of the device may be rounded, e.g. dome-like or hemispherical.

The instrument may comprises an imaging element for conveying an imaging signal to permit visualisation of a distal end of the instrument. In an embodiment, the imaging element may include a fibrescope comprising a bundle of optical fibres. The bundle of optical fibres may have a diameter of 0.3 mm to 0.5 mm, and may contain both illumination and detection fibres. Suitable fiberscopes are manufactured by Fujikura and can provide images with up to 10,000 pixels. The inner conductor and distal conductive portion may be hollow to define a channel for carrying the bundle of optical fibres. Alternatively, the bundle of optical fibres may be integrally formed with the inner conductor and distal conductive portion. For example, the bundle of fibres may extend through the first dielectric material and radiating tip portion and may have a layer of conductive material over its outer surface, whereby it actually forms the inner conductor of the coaxial cable and the distal conductive portion.

In an alternative embodiment, the imaging element may comprise a image sensor mounted at the distal end of the radiating tip portion and a communication cable for conveying a signal from the image sensor to the proximal end of the instrument. The image sensor may be CMOS- or CCD-based. The communication cable may include one or more optical fibres for conveying an illumination signal. In another embodiment, the image sensor may include an ultrasound transducer. Similarly to the arrangement discussed above, the inner conductor and distal conductive portion may be hollow to define a channel for carrying the communication cable.

In other embodiments, the bundle of optical fibres or communication cable may be offset from the axis of the coaxial cable. For example, the bundle of optical fibres or the communication cable may run alongside the coaxial cable or may be integrated within an outer sheath or catheter that surrounds the instrument.

In order to obtain better image resolution, there may be a plurality of image sensors mounted at the distal end of the instrument. A plurality of optical fibre bundles may convey the image data to the proximal end of the instrument.

The instrument may further include a temperature sensor at the distal end thereof. The instrument can therefore provide additional feedback about the conditions at the distal end of the instrument. The temperature sensor may be a thermocouple mounted on the outer conductor of the coaxial cable. The thermocouple may have a plurality of stubs formed therewith, the stubs being arranged to filter out a signal having the same frequency as the microwave energy.

Alternatively, the temperature sensor may be combined with the imaging element discussed above. For example, the temperature sensor may include a temperature sensitive micromechanical structure at the distal end of the end. The imaging element or some other means may be used to optically monitor the temperature sensitive micromechanical structure and thereby derive information indicative of temperature conditions at the distal end of the instrument.

The microwave energy may be applied in a pulsed manner. To avoid the microwave energy from swamping response signal from the temperature sensor, temperature measurements may be taken when the microwave energy is off, i.e. in an OFF period of the pulsed operation. Alternatively or additionally, the instrument may include a filtering arrangement for removing noise on the response signal from the temperature sensor caused by the microwave energy. The filtering arrangement may include a low pass filter and a common mode injection instrumentation amplifier arranged to remove higher frequency components from the response signal.

The whole instrument may be mounted in a closed end catheter or outer sheath. The outer sheath may be a multi lumen catheter arranged to convey any one or more of: guide wires for controlling movement of the radiating tip section, and fluid for cooling the distal end of the instrument. By providing guide wires to control movement of the instrument, it may be possible to navigate inside the bronchial tree to locate and treat tumours that cannot currently be treated. The guide wires may run inside the outer sheath or can be extruded as an integral part of it. One, two or three guide wires may be used.

In another aspect, the invention provides an electrosurgical apparatus for delivering microwave energy into lung tissue, the electrosurgical apparatus comprising: a generator for generating microwave energy; a bronchoscope for non-percutaneous insertion into a patient's lungs, the bronchoscope having an instrument channel running along its length; and an electrosurgical instrument as set out above in the instrument channel of the bronchoscope, wherein the coaxial cable is connected to receive microwave energy from the generator. The generator may be arranged to deliver pulses of microwave energy in time with the breathing cycle of the patient.

In a further aspect, the invention provides a bronchoscope comprising: a body; and a flexible instrument cord for non-percutaneous insertion to a patient's lungs, the instrument cord extending from the body and having an longitudinally extending instrument channel formed therethrough, wherein the body includes: a power input port that is connectable to receive microwave energy, and a optical port arranged to receive optical signals from a distal end of the instrument cord, and wherein the instrument cord comprises a coaxial transmission line formed around the instrument channel, the coaxial transmission line being connected to the power input port to convey microwave energy to the distal end of the instrument cord. In this aspect, the means for delivery power is integrated into the instrument cord of the bronchoscope as opposed to being delivered in a coaxial cable that runs through the instrument channel thereof. This enables a large coaxial structure to be used within the same overall instrument cord diameter. In turn this can reduce losses and/or free up space in the instrument channel for other uses.

The bronchoscope may have a radiator mounted at a distal end of the instrument channel, the radiator being electrically connected to the coaxial transmission line to receive microwave energy therefrom and emit a microwave field. The radiator may be an electrosurgical instrument as described above, e.g. with a section of coaxial cable that protrudes from the instrument cord and terminates at a radiating tip. The outer diameter of the coaxial transmission line may be greater than the outer diameter of the coaxial cable in the electrosurgical instrument. In other word the overall power delivery structure comprises a pair of coaxial lines having differing diameters.

The bronchoscope with integrated coaxial transmission line may be used with other types of radiator. For example, the radiator may comprise any one of: an expandable balloon, a radially expanding tube, a forceps structure, and a paddle structure.

The instrument channel (or another dedicated channel in the instrument cord) may be arranged to receive fluid (e.g. a coolant such as saline or water) for cooling the coaxial transmission line during treatment. The body may therefore comprise a fluid input port, the fluid input port being in communication with the instrument channel (or another lumen in the instrument cord).

The body may include a control actuator connected to one or more guide wires, the guide wires extending through the instrument cord to the radiator, wherein the control actuator is operable to move the guide wires within the instrument cord to control movement of the radiator. The guide wires may extend through the instrument channel or through other dedicated passageways in the instrument cord.

The body may include an illumination port and the instrument cord may include one or more optical channels in optical communication with the illumination port for conveying an illumination signal to the distal end thereof to illuminate a treatment region. The illumination signal may be optical radiation (e.g. white light) for enabling the treatment region to be viewing through the optical port (e.g. eye piece). Alternatively or additionally, the illumination signal may enable images of the treatment region to be captured.

In one example, the illumination signal may be for spectroscopic purposes. It may by from a UV laser, for example.

A light source may be mounted to the body to generate the illumination signal. The light source may be an LED or halogen light source.

In another aspect, the invention provides an electrosurgical apparatus for delivering microwave energy into lung tissue, the electrosurgical apparatus comprising: a generator for generating microwave energy; and a bronchoscope as described above, wherein the power input port is connected to the generator to convey the microwave energy to the coaxial transmission line. The generator may be arranged to pulse the microwave energy with a duty cycle between 1% and 50%.

Herein, radiofrequency (RF) may mean a stable fixed frequency in the range 10 kHz to 300 MHz and microwave frequency may mean a stable fixed frequency in the range 300 MHz to 100 GHz. Preferred spot frequencies for the RF energy include any one or more of: 100 kHz, 250 kHz, 400 kHz, 500 kHz, 1 MHz, and 5 MHz. Preferred spot frequencies for the microwave energy include 915 MHz, 2.45 GHz, 5.8 GHz, 14.5 GHz, and 24 GHz.

Herein, the term "conductive" means "electrically conductive" unless the context dictates otherwise.

BRIEF DESCRIPTION OF DRAWINGS

Examples of the invention are described in more detail below with reference to the accompanying drawings, in which.

DETAILED DESCRIPTION; FURTHER OPTIONS AND PREFERENCES

Figure 1:
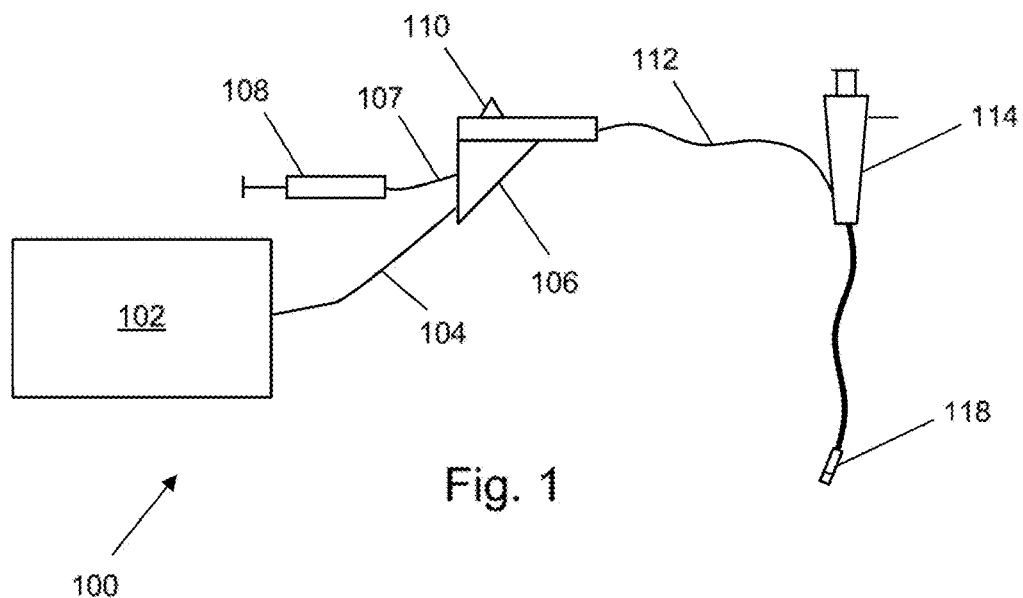
FIG. 1 is a schematic diagram of an electrosurgical apparatus with which the present invention can be used.

FIG. 1 is a schematic diagram of a complete electrosurgery system 100 that is capable of supplying microwave energy and fluid, e.g. cooling fluid, to the distal end of an invasive electrosurgical instrument. The system 100 comprises a generator 102 for controllably supplying microwave energy. A suitable generator for this purpose is described in WO 2012/076844, which is incorporated herein by reference. The generator may be arranged to monitor reflected signals received back from the instrument in order to determine an appropriate power level for delivery. For example, the generator may be arranged to calculate an impedance seen at the distal end of the instrument in order to determine an optimal delivery power level. The generator may be arranged to deliver power in a series of pulses which are modulated to match a patient's breathing cycle. This will allow for power delivery to occur when the lungs are deflated.

The generator 102 is connected to an interface joint 106 by an interface cable 104. The interface joint 106 is also connected to receive a fluid supply 107 from a fluid delivery device 108, such as a syringe. If needed, the interface joint 106 can house an instrument control mechanism that is operable by sliding a trigger 110, e.g. to control longitudinal (back and forth) movement of one or more control wires or push rods (not shown). If there is a plurality of control wires, there may be multiple sliding triggers on the interface joint to provide full control. The function of the interface joint 106 is to combine the inputs from the generator 102, fluid delivery device 108 and instrument control mechanism into a single flexible shaft 112, which extends from the distal end of the interface joint 106.

The flexible shaft 112 is insertable through the entire length of an instrument (working) channel of a bronchoscope 114.

The flexible shaft 112 has a distal assembly 118 (not drawn to scale in FIG. 1) that is shaped to pass through the instrument channel of the bronchoscope 114 and protrude (e.g. inside the patient) at the distal end of the bronchoscope's tube. The distal end assembly includes an active tip for delivering microwave energy into biological tissue. The tip configuration is discussed in more detail below.

The structure of the distal assembly 118 discussed below may be particularly designed for use with a conventional steerable flexible bronchoscope, whereby the maximum outer diameter of the distal assembly 118 is equal to or less than 2.5 mm, and preferably less than 1.9 mm (and more preferably less than 1.5 mm) and the length of the flexible shaft can be equal to or greater than 1.2 m.

The apparatus described above is one way of introducing the instrument. Other techniques are possible. For example, the instrument may also be inserted using a catheter.

The invention seeks to provide an instrument that can deliver microwave energy to tissue, particularly to the lungs. In order for side effects to be reduced and the efficiency of the instrument to be maximised, the transmitting antenna should be located as close to the target tissue as possible. Ideally, the radiating part of the instrument is located inside (e.g. at the centre of) the tumour during treatment. In order to reach the target site within the lungs, the instrument will need to be guided through the airways and around obstacles such as the vocal chords. This means that the instrument will ideally be flexible and have a small cross section. Particularly, the instrument should be very flexible near the antenna where it needs to be steered along bronchioles which can be narrow and winding. The size of the antenna part of the instrument should also be reduced where possible to allow the antenna to work properly in small locations and increase flexibility of the instrument when components of the antenna are rigid. As discussed below, the instrument may comprise two coaxial transmission lines arranged in series, with a proximal coaxial transmission line having a greater outer diameter than a distal coaxial transmission line. The outer diameter of the proximal coaxial transmission line may be equal to or greater than 2 mm and the outer diameter of the distal coaxial transmission line may be equal to or less than 1.5 mm, e.g. 1.2 mm. The proximal coaxial transmission line may extend along the majority of the flexible shaft. For example, proximal coaxial transmission line may have a length of 1 m and the distal coaxial transmission line may have a length equal to or less than 0.3 m. This arrangement can ensure that more microwave power is delivered into the tissue without the proximal coaxial transmission line getting too hot.

Another way of avoiding unwanted heating of the cable is to deliver the microwave energy in a pulsed manner. In one example, the microwave energy can be delivered with a duty cycle of 9%, e.g. a 110 ms period consisting of a 10 ms ON portion and a 100 ms OFF portion. The duty cycle may be less than 9%, e.g. 5%.

Heating of the cable can also be mitigated by providing cooling fluid.

The cable for delivering the microwave radiation to the target site should be low-loss, have a small cross-section and be flexible. The cable should be low loss to avoid heating during treatment and so that there is enough power at the distal end to produce the desired radiation from the antenna.

If the cable is not separated from the body by the use of a sealed bronchoscope, catheter or other protective sheath when in use, then the cable should be made of biologically inert material to avoid unwanted interaction with the body.

A preferred cable type is a coaxial cable which is made up of an inner conductor axially surrounded by a dielectric sheath which is in turn axially surrounded by an outer conductor. The radiating portion in an antenna produced from such a cable may be made up of a section of inner conductor and dielectric sheath which protrudes from the end of the outer conductor of the coaxial cable.

The invention also seeks to provide an antenna with a well-defined radiation pattern. It is desirable that a practitioner would be able to select an instrument for the treatment of a specific area of tissue, such that the radiation of target tissue is maximised and the radiation of healthy tissue is minimised. For example, in some circumstances it can be desirable to produce a generally spherically symmetric radiation pattern with a substantially uniform power absorption distribution, so that the amount of radiation received by an area of tissue can be more easily controlled by the practitioner. However, in other circumstances it may also be desirable to restrict the radiation to one side of the instrument, to avoid unnecessary radiation of healthy tissue on the other side of the instrument. For example, such a configuration may be used when the target tissue is on only one side of the airway in which the instrument is positioned for treatment.

It is also preferable that the instrument can be operated alongside other instruments to enable practitioners to receive information from the target site. For example, a bronchoscope may aid the steering of the instruments around obstacles such as the vocal chords. Other instruments may include a thermometer or camera.

In the following description, unless stated otherwise, the length of a component refers to its dimension in the direction parallel to the longitudinal axis of the coaxial cable.

Figure 2:
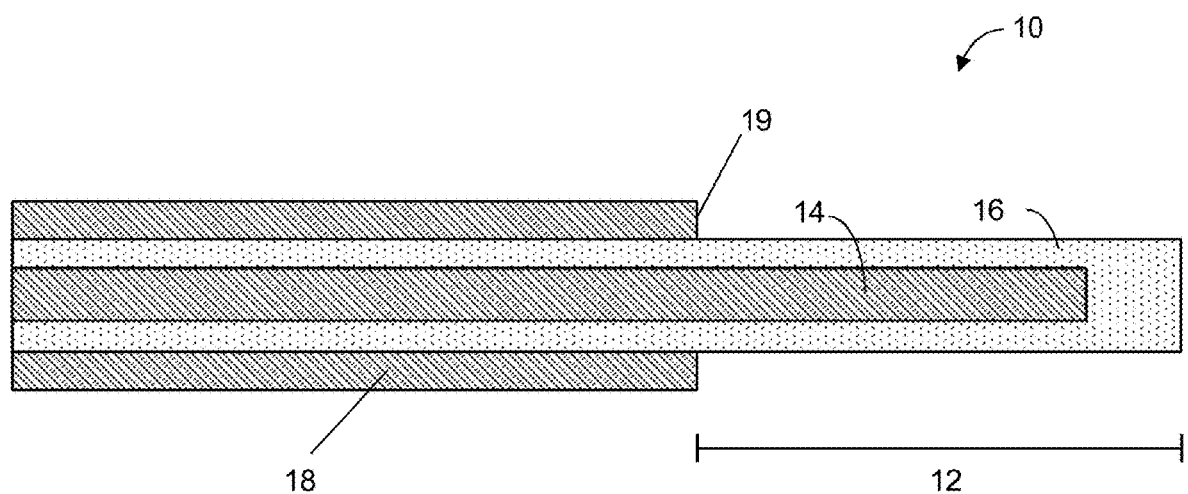
FIG. 2 is a longitudinal cross section of a electrosurgical device that can be used in embodiments of the invention.

FIG. 2 is a longitudinal cross section taken along the axis of a coaxial cable which forms a tissue ablation antenna 10. The tissue ablation antenna comprises a radiating portion 12. The inner conductor 14 is radially surrounded by the dielectric sheath 16 which is in turn radially surrounded by the outer conductor 18. The inner conductor 14 and the insulating sheath 16 extend beyond a distal end 19 of the outer conductor 18 and the protruding section of inner conductor and insulating sheath forms the radiating portion 12. In this example, the inner conductor 14 is shorter than the insulating sheath 16 so that the end of the insulating sheath 16 forms a cap over the inner conductor 14.

Figure 5A:
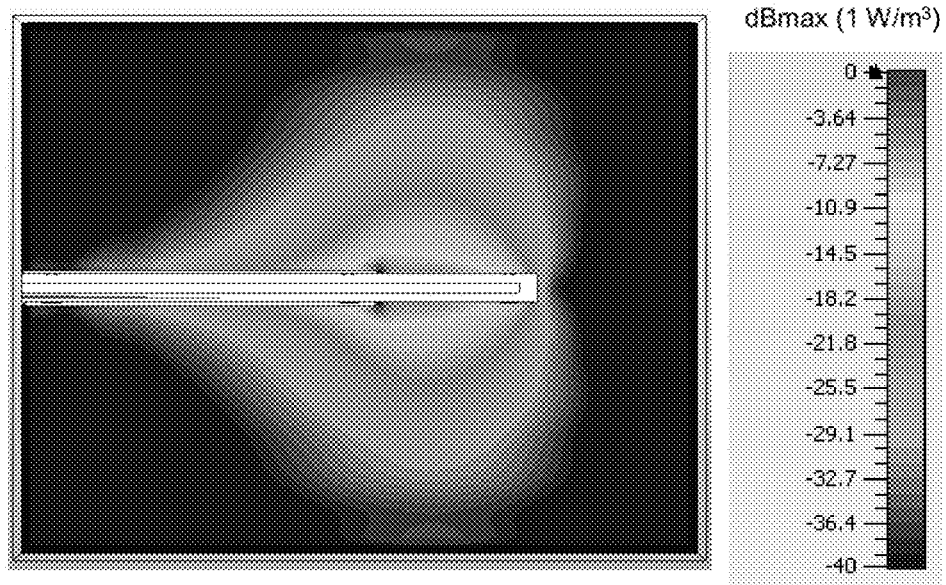
FIG. 5A is a longitudinal cross section of a simulation of the radiation absorption pattern produced by the electrosurgical device of FIG. 1.
Figure 5B:
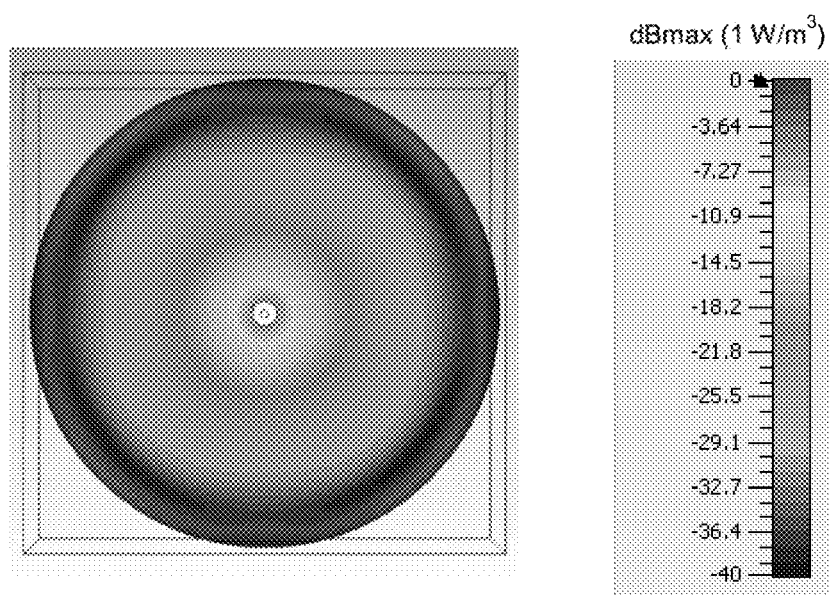
FIG. 5B is an axial cross section of a simulation of the radiation absorption pattern produced by the electrosurgical device of FIG. 1.

FIGS. 5A and 5B show longitudinal and axial cross-sections respectively of a radiation pattern simulation for the antenna 10 shown in FIG. 2. It can be seen that the pattern covers an elongated region near the end of the outer conductor 18. It is axially symmetric and is generally strongest at the distal end 19 of the outer conductor 18.

Figure 3:
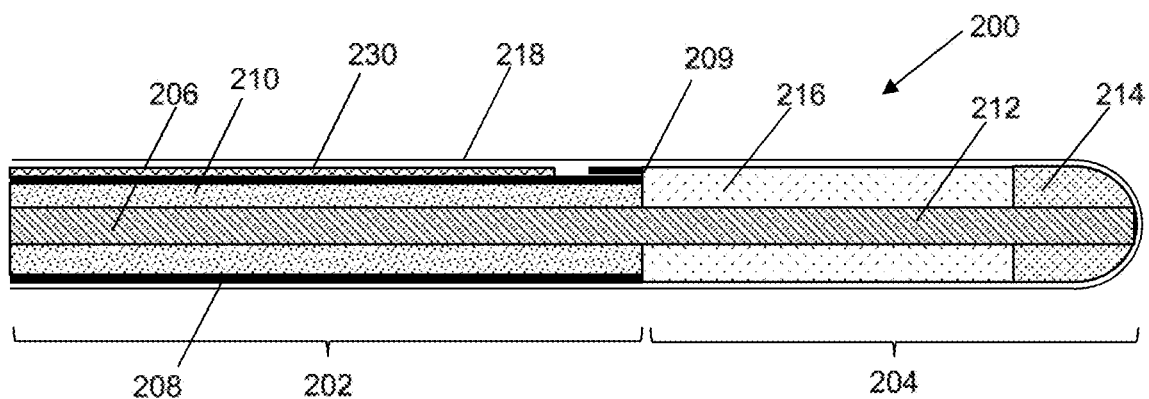
FIG. 3 is a longitudinal cross section of an electrosurgical device that is an embodiment of the invention.

FIG. 3 is a cross-sectional view of the distal end of an electrosurgical instrument 200 that is an embodiment of the invention. The electrosurgical instrument 200 comprises a coaxial cable 202 that is connected at its proximal end to a electrosurgical generator (not shown) in order to convey microwave energy. The coaxial cable 202 comprises an inner conductor 206, which is separated from an outer conductor 208 by a first dielectric material 210. The coaxial cable 202 is preferably low loss for microwave energy. A choke (not shown) may be provided on the coaxial cable to inhibit back propagation of microwave energy reflected from the distal end and therefore limit backward heating along the device.

The device may include a temperature sensor at the distal end. For example, in FIG. 3 a thermocouple 230 is mounted on the outer conductor to transmit a signal back to the proximal end that is indicative of temperature at the distal end of the instrument. This type of temperature sensor is discussed in more detail below with reference to FIGS. 18 to 20.

Other techniques for temperature monitoring can be used. For example, one or more micromechanical structure whose physical configuration is sensitive to temperature may be mounted in the distal portion of the device, e.g. in or on the outer sheath discussed below. These structures can be interfaced with an optical fibre, whereby changes in a reflected signal caused by movement of the structure can be indicative of temperature changes.

The coaxial cable 202 terminates at its distal end with a radiating tip section 204. In this embodiment, the radiating tip section 204 comprises a distal conductive section 212 of the inner conductor 206 that extends before a distal end 209 of the outer conductor 208. The distal conductive section 212 is surrounded at its distal end by a dielectric tip 214 formed from a second dielectric material, which is different from the first dielectric material 210. The length of the dielectric tip 214 is shorter than the length of the distal conductive section 212. An intermediate dielectric sleeve 216 surrounds the distal conductive section 212 between the distal end of the coaxial cable 202 and the proximal end of the dielectric tip 214. The intermediate dielectric sleeve 216 is formed from a third dielectric material, which is different from the second dielectric material but which may be the same as the first dielectric material 210.

In this embodiment, the coaxial cable 202 and radiating tip section 204 have an outer sheath 218 formed over their outermost surfaces. The outer sheath 218 may be formed from a biocompatible material. The outer sheath 218 has a thickness that is small enough to ensure that it does not significantly interfere with the microwave energy radiated by the radiating tip section 204 (i.e. radiating pattern and return loss). In an embodiment, the sheath is made from PTFE, although other materials are also appropriate. The thickness of the wall of the sheath is selected to be withstand breakdown voltages equal to or greater than 500 V (peak).

The purpose of the dielectric tip 214 is to alter the shape of the radiated energy. The second dielectric material is selected to reduce the wavelength of the microwave energy, which results in the radiated energy exhibiting a more spherical radiation pattern. To do this, the second dielectric material preferably has a large dielectric constant (relative permittivity). The dielectric constant of the second dielectric material is preferably chosen to enable the length of the dielectric tip 214 to be minimised whilst still constituting a non-negligible portion of a wavelength of the microwave energy when it propagates through the second dielectric material. It is desirable for the dielectric tip to be as short as possible in order to retain flexibility in the device, especially if the second dielectric material is rigid. In an embodiment, the dielectric tip may have a length equal to or less than 2 mm. The dielectric constant of the second dielectric material may be greater than 80, and is preferably 100 or more at the frequency of the microwave energy. The second dielectric material may be $TiO_2$ (titanium dioxide).

The wavelength of radiation in a material becomes shorter as the dielectric constant of the material increases. Therefore a dielectric tip 214 with a greater dielectric constant will have a greater effect on the radiation pattern. The larger the dielectric constant, the smaller the dielectric tip 214 can be while still having a substantial effect on the shape of the radiation pattern. Using a dielectric tip 214 with a large dielectric constant means that the antenna can be made small and so the instrument can remain flexible. For example the dielectric constant in $TiO_2$ is around 100. The wavelength of microwave radiation having a frequency of 5.8 GHz is about 6 mm in $TiO_2$ compared to around 36 mm in PTFE (which may be the material used for the first and/or third dielectric materials). A noticeable effect on the shape of the radiation pattern can be produced in this arrangement with a dielectric tip 214 of approximately 1 mm. As the dielectric tip 214 is short, it can be made from a rigid material whilst still maintaining flexibility of the antenna as a whole. The dielectric tip 214 may have any suitable distal shape. In FIG. 3 it has a dome shape, but this is not necessarily essential. For example, it may be cylindrical, conical, etc. However, a smooth dome shape may be preferred because it increases the mobility of the antenna as it is manoeuvred through small channels. The dielectric tip 214 may be coated with a non-stick material such as Parylene C or Parylene D, or PFTE to prevent the tissue from sticking to the instrument. The whole instrument can be coated in this way.

The properties of the intermediate dielectric sleeve 216 are preferably chosen (e.g. through simulation or the like) so that the radiating tip section 204 forms a quarter wave impedance transformer for matching the input impedance of the generator into a biological tissue load in contact with the radiating tip section 204.

Figure 6:
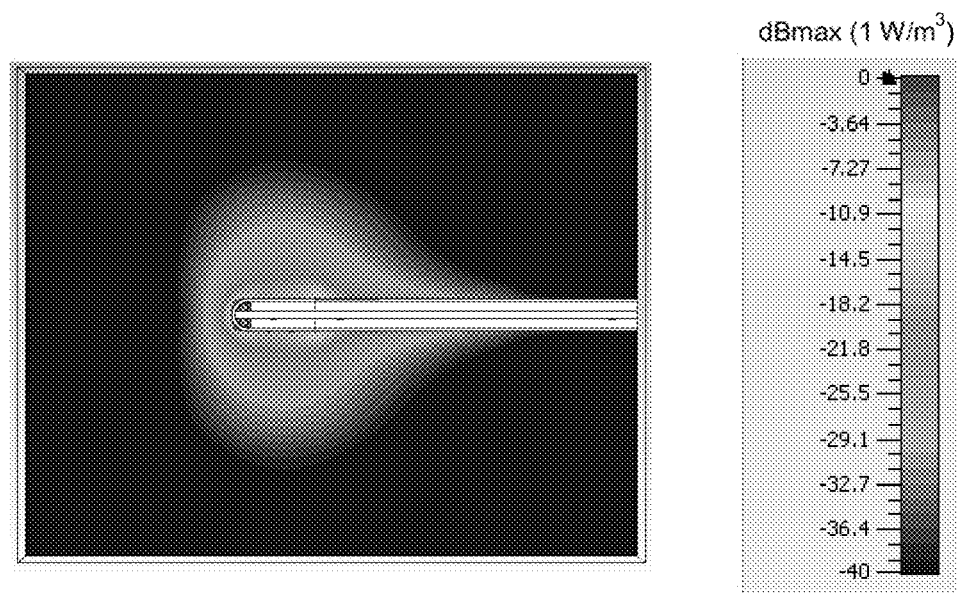
FIG. 6 is a longitudinal cross section of a simulation of the radiation absorption pattern produced by the electrosurgical device of FIG. 3.

A longitudinal cross section of a simulation of the absorption pattern of an antenna having the configuration shown in FIG. 3 is shown in FIG. 6. The pattern produced is more uniform and more spherical than the pattern shown in FIGS. 5A and 5B. The pattern in FIG. 6 is axially symmetric and more of the radiation is concentrated around the radiating portion rather than spreading down the cable as occurs in FIGS. 5A and 5B. This means that, when in use, an area of tissue may be radiated more uniformly, meaning there is less chance of damage to healthy tissue. The radiation is also less spread out, allowing the practitioner to more accurately radiate target tissue and reduce radiation of or damage to healthy tissue. The pear drop shape of radiation pattern shown in FIG. 6 may also be particularly useful for treating fibroids.

During treatment, the surrounding tissue absorbs the radiated energy. The volume of tissue into which the energy is delivered depends on the frequency of the microwave energy.

Figure 4:
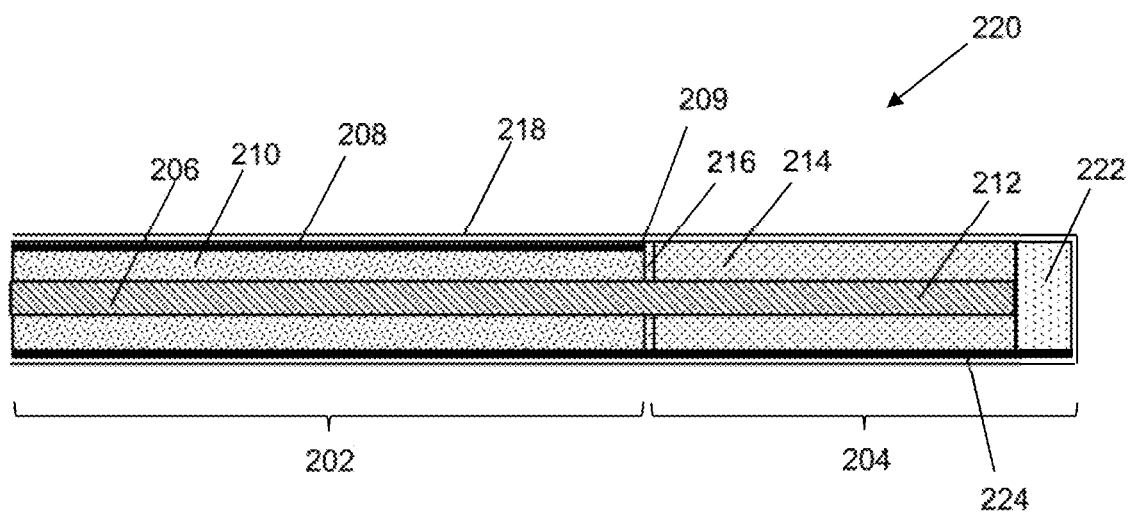
FIG. 4 is a longitudinal cross section of an electrosurgical device that is an embodiment of the invention.

FIG. 4 is a cross-sectional view of the distal end of an electrosurgical instrument 220 that is another embodiment of the invention. Components in common with electrosurgical instrument 200 shown in FIG. 3 are given the same reference numbers and are not described again.

In this embodiment the radiating tip section 204 is configured differently. The intermediate dielectric sleeve 216 is a short collar having a length much less than the dielectric tip 214. However, the dielectric tip 214 acts in the same manner as described above with respect to FIG. 3 in that it shortens the wavelength of the microwave energy to provide a more focussed field.

A dielectric cap 222 formed of a fourth dielectric material, which is different from the second dielectric material but may be the same as the first or third dielectric material 210 is formed at the distal end of the dielectric tip 214. Similarly to FIG. 3, the second dielectric material may be TiO$_2$ and the third dielectric material may be PFTE. The fourth dielectric material may also be PTFE.

FIG. 4 is not drawn to scale. The length of the dielectric tip 214 may be similar to that discussed above, e.g. less than 3 mm, preferably less than 2 mm. The length of the dielectric cap 222 may be shorter than the length of the dielectric tip 214. For example, it may be equal to or less than 1 mm. In both FIGS. 3 and 4 it is desirable for the maximum outer diameter of the instrument to be equal to or less than 3 mm, preferably equal to or less than 1.9 mm, although the invention need not be limited to these dimensions.

In this embodiment a portion of the outer conductor 208, e.g. a narrow strip or conductive finger 224 extends beyond the coaxial cable 202. The conductive finger 224 acts as a field reflector to cause the radiating field to be directed out of the side of the radiating tip that is opposite to the conductive finger 224.

The dielectric cap 222 is provided to enable the conductive finger to extend beyond the distal end of the distal conductive portion 212 formed by the inner conductor 206. This configuration has been found to improve the impedance matching function of the radiating tip section 204.

In a specific example of the structure shown in FIG. 4, the conductive finger 224 may extend by a length of 3.6 mm beyond the distal end of the coaxial cable. The dielectric tip 214 may have a length of 2.5 mm and may be made from TiO$_2$. The distal conductive portion 212 of the inner conductor 206 may protrude 2.6 mm from the end of the coaxial cable 202, so the intermediate dielectric sleeve 216 may have a length of 0.1 mm. With this configuration, the conductive finger 224 extends 1 mm past the distal end of the distal conductive portion 212, which improves the effectiveness of its reflecting function. The dielectric cap 222 has a length of 1 mm. The dimensions given here relate to a specific example that is based on a certain dielectric constant value. For other dielectric materials, the dimensions may change accordingly.

As this antenna is so short, it is easier to introduce into tightly curved tubes and can be guided through small lung airways to get close to target sites.

Figure 7A:
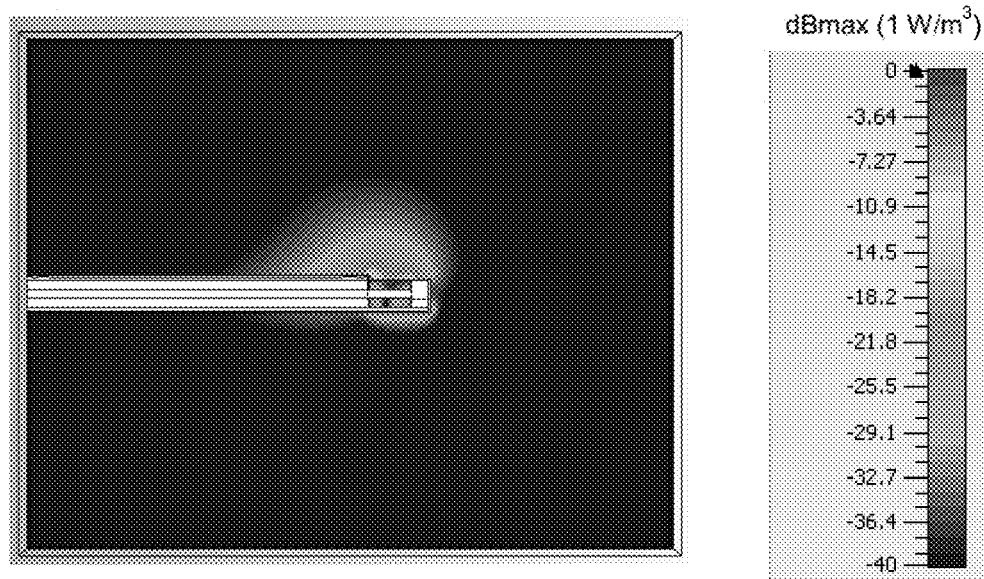
FIG. 7A is a first longitudinal cross section of a simulation of the radiation absorption pattern produced by the electrosurgical device of FIG. 4.
Figure 7B:
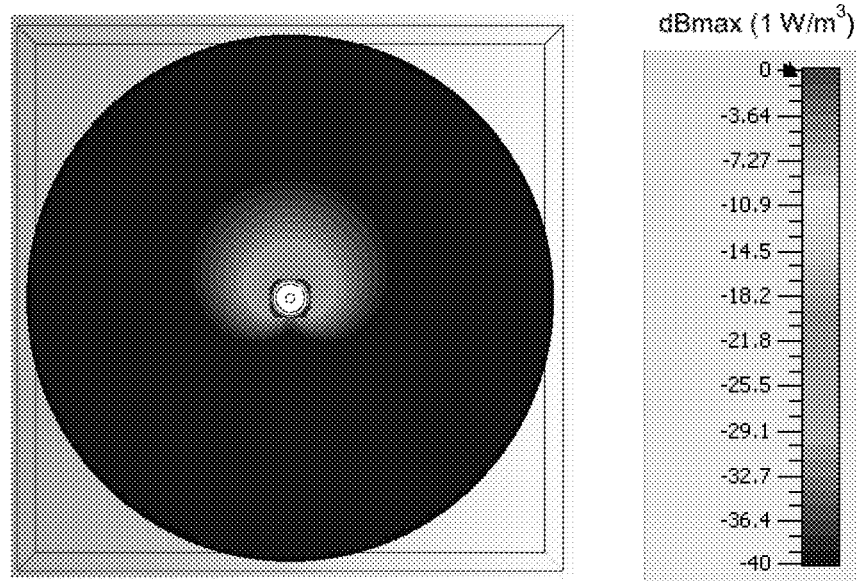
FIG. 7B is an axial cross section of a simulation of the radiation absorption pattern produced by the electrosurgical device of FIG. 4.
Figure 7C:
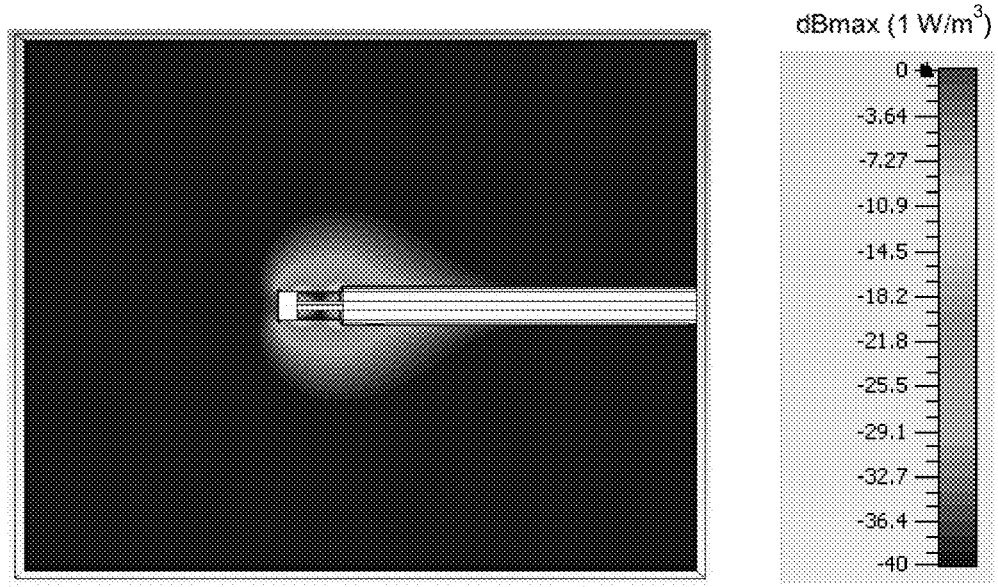
FIG. 7C is a second longitudinal cross section of a simulation of the radiation absorption pattern produced by the electrosurgical device of FIG. 4.

FIGS. 7A, 7B and 7C shows various views of simulated absorption of microwave energy radiated by the antenna structure shown in FIG. 4.

FIG. 7A shows a longitudinal cross section of the simulated absorption. Much more radiation is emitted from the side of the antenna that is opposite to the conductive finger 224. FIG. 7B shows an axial view of the simulated absorption that shows a similar effect.

FIG. 7C shows a longitudinal cross section of the simulated absorption when looking directly at the side opposite the conductive finger, which shows how the shape of the field is changed by the choice of material for the dielectric tip 214.

Figure 8A:
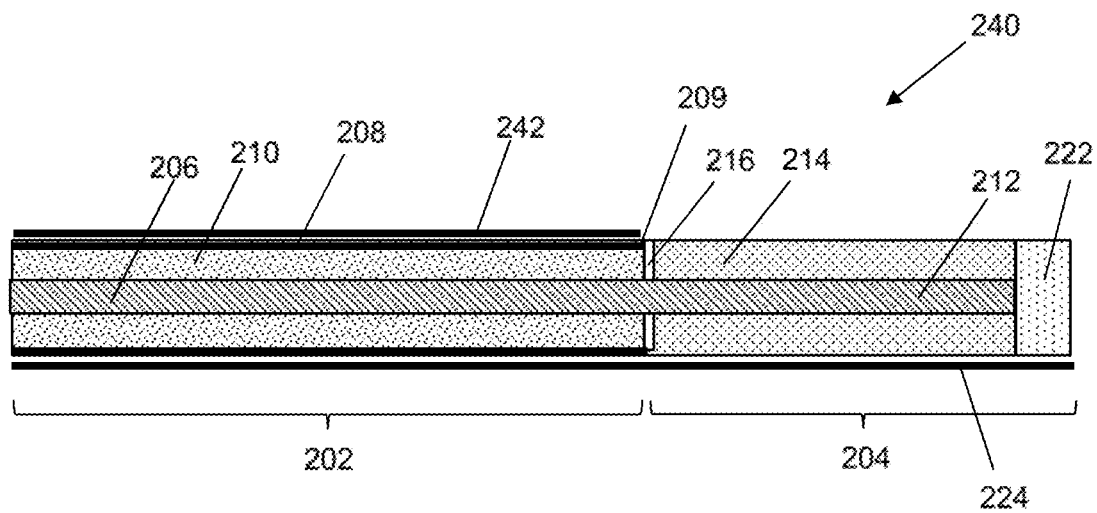
FIG. 8A is a longitudinal cross section of an electrosurgical device that is an embodiment of the invention.

FIG. 8A is a cross-sectional view of the distal end of an electrosurgical instrument 240 that is another embodiment of the invention. Components in common with electrosurgical instrument 220 shown in FIG. 4 are given the same reference numbers and are not described again.

In this embodiment the conductive finger 224 is not provided as an extension of the outer conductor 208. Instead, it is formed as part of an electrically conductive sleeve 242 that is mounted over at least a distal portion of the coaxial cable 202. The electrically conductive sleeve 242 is electrically connected to the outer conductor 208, e.g. by an interference fit. In this embodiment, the electrically conductive sleeve 242 is rotatable relative to the coaxial cable 202 and radiating tip section 204. This allows the location of the conductive finger 224 to be varied around the circumference of the radiating tip section without having to twist the whole instrument.

Figure 8B:
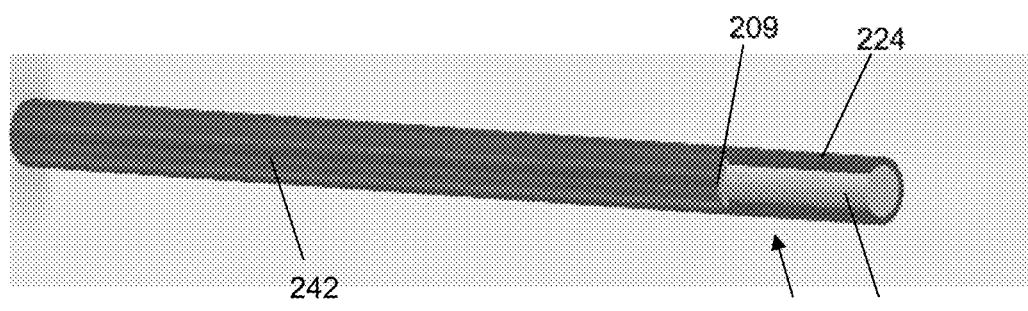
FIG. 8B is a schematic isometric view of a first variant of the electrosurgical device shown in FIG. 8A.

The conductive finger 224 may be configured in various ways. FIG. 8B shows a first variant, in which the conductive finger 224 surrounds a majority of the circumference of the radiating tip section 204, thereby defining a longitudinal slot 244 through which the dielectric tip 214 is exposed to enable the microwave energy to be radiated.

Figure 8C:
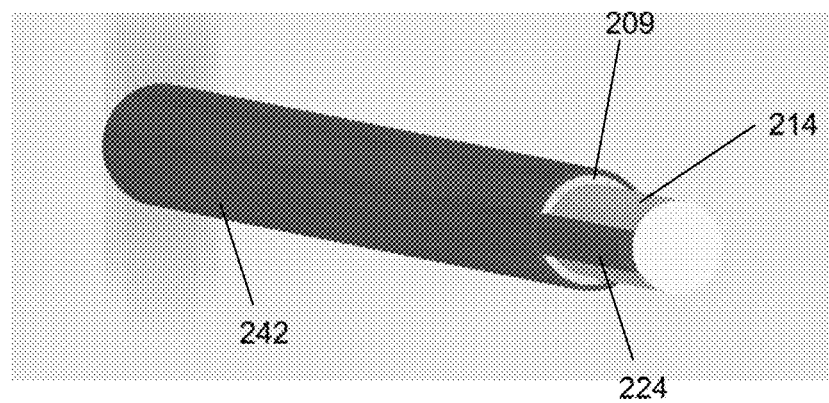
FIG. 8C is a schematic isometric view of a second variant of the electrosurgical device shown in FIG. 8A.

FIG. 8C shows a second variant, in which the conductive finger 224 is a narrow elongate strip extending from the rest of the electrically conductive sleeve 242.

Figure 9A:
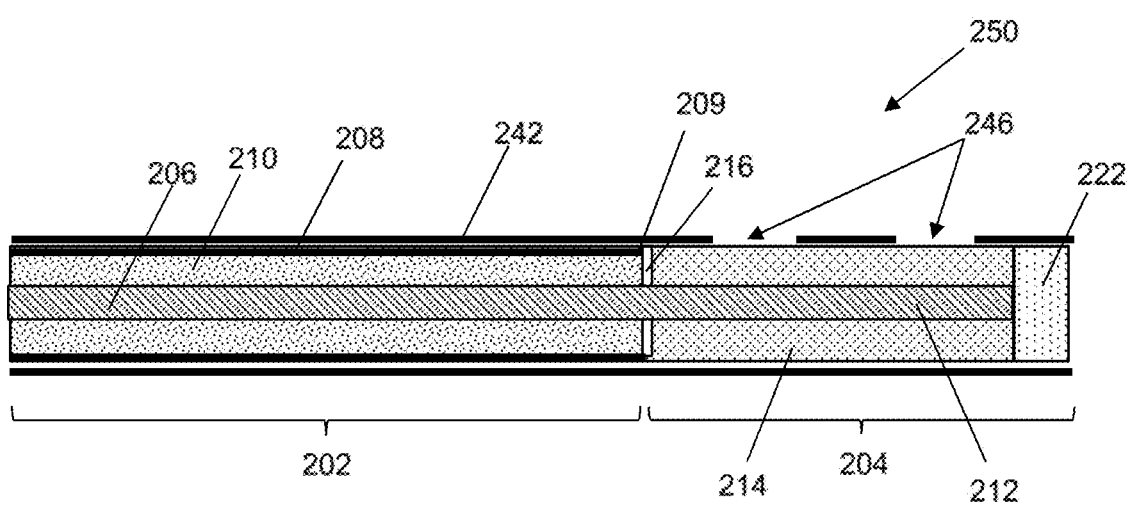
FIG. 9A is a longitudinal cross section of an electrosurgical device that is an embodiment of the invention.

FIG. 9A is a cross-sectional view of the distal end of an electrosurgical instrument 250 that is another embodiment of the invention. Components in common with electrosurgical instrument 240 shown in FIG. 8A are given the same reference numbers and are not described again.

Figure 9B:
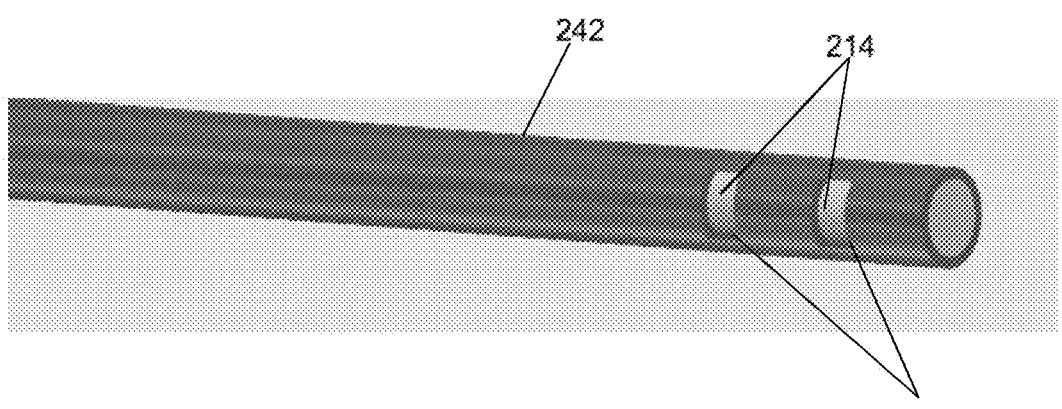
FIG. 9B is a schematic isometric view of the electrosurgical device shown in FIG. 9A.

In this embodiment, instead of defining the conductive finger 224, the rotatable electrically conductive sleeve 242 extends to the distal end of the radiating tip section 204 but has one or more slots 246 (two in this example) formed in it to expose the dielectric tip 214 to enable the microwave energy to be radiated. FIG. 9B illustrates the outward appearance of this arrangement.

If the distal end of the instrument is arranged as an open circuit, the slots may be located at multiples of a half wavelength of the microwave energy from the distal end. If the distal end is arranged as a short circuit, the distal-most slot would be located at a quarter wavelength of the microwave energy from the distal end, with subsequent slots being separated from the first slot by multiples of a half wavelength of the microwave energy. Where the slot lie over the second dielectric material, it is the reduced wavelength of the microwave energy in that dielectric material that is used to calculate the position of the slots.

In another variant of this embodiment, the rotatable electrically conductive sleeve is omitted and instead the outer conductor extends to cover the radiating tip section 214 and the slot(s) are formed in the outer conductor.

In other unillustrated embodiments, different types of radiating structure may be provided at the radiating tip section 204 to enable microwave energy to be launched into tissue. For example, patch antennas could be provided by fabricating conductive structures on, e.g. partially metallizing, the outer surface of the dielectric tip 214. Alternatively, the dielectric tip 214 may be configured to include a microstrip line or coplanar antenna structure that is connected to receive power from the coaxial cable 102.

Figure 10A:
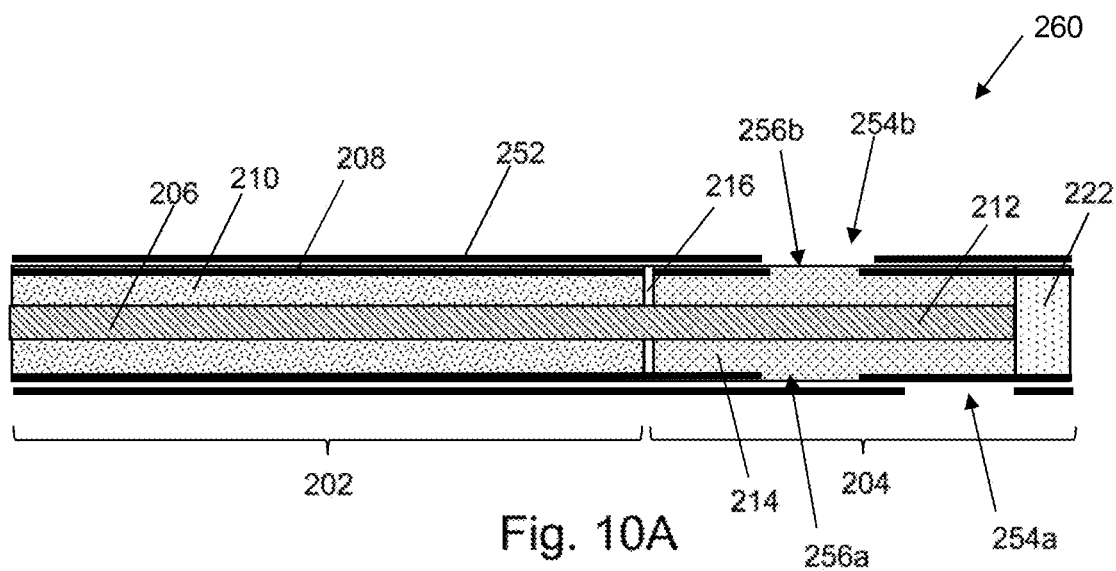
FIG. 10A is a longitudinal cross section of an electrosurgical device that is an embodiment of the invention.

FIG. 10A is a cross-sectional view of the distal end of an electrosurgical instrument 260 that is another embodiment of the invention. Components in common with electrosurgical instrument 240 shown in FIG. 8A are given the same reference numbers and are not described again.

In this embodiment the outer conductor 208 extends to the distal end of the radiating tip section 204 and has a pair of diametrically opposed slots 256*a*, 256*b* formed therein to expose the dielectric tip 214. An axially slidable electrically conductive sleeve 252 is mounted over at least a distal portion of the coaxial cable 202 and the radiating tip section 204. The electrically conductive sleeve 252 is conductively connected to the outer conductor 208 such that they are effectively the same conductive body. The electrically conductive sleeve 252 has a pair of slots 254*a*, 254*b* formed on opposite sides thereof. However, unlike the slots 256*a*, 256*b* on the outer conductor 208, the slots 254*a*, 254*b* are axially offset from each other. Each of the slots 254*a*, 254*b* is circumferentially aligned with a respective one of the slots 256*a*, 256*b*, so that the dielectric tip can be exposed when each slot 254*a*, 254*b* is axially aligned with its respective slot. Accordingly, in use, the axial position of the electrically conductive sleeve 252 can be selected so that only one of the slots 256*a*, 256*b* is in line with its respective slot 254*a*, 254*b*, whereby the lateral direction in which microwave energy is radiated from the dielectric tip can be selected using a purely axial (longitudinal) actuation motion.

Figure 10B:
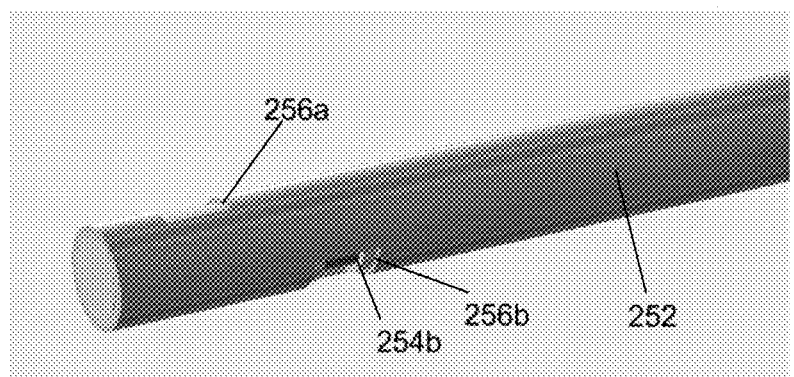
FIG. 10B is a schematic isometric view of the electrosurgical device shown in FIG. 10A is a first configuration.
Figure 10C:
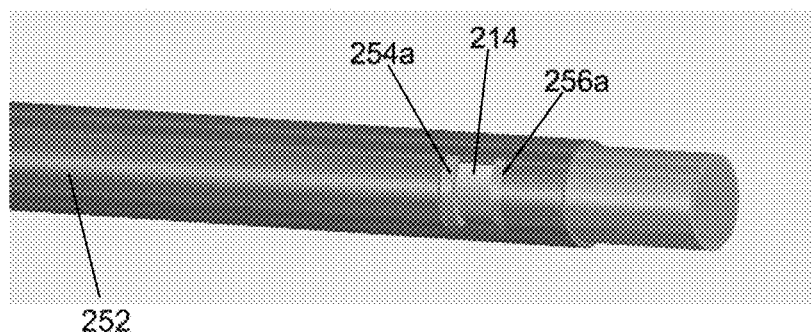
FIG. 10C is a schematic isometric view of the electrosurgical device shown in FIG. 10A is a second configuration.

FIG. 10B shows the axially slidable electrically conductive sleeve 252 in a forward position in which its rearward slot 256*b* is aligned with a first slot 254*b* on the outer conductor 208. FIG. 10C shows the axially slidable electrically conductive sleeve 252 in a retracted position in which its forward slot 256*a* is aligned with a second slot 254*a* on the outer conductor 208.

The axially slidable electrically conductive sleeve 252 may be moved between the forward and retracted positions by control wires or push rods (not shown) that pass along the instrument channel of the bronchoscope to an actuator (not shown) at the proximal end of the instrument channel.

In any of the embodiments discussed above, it may be desirable to include a vision system. For example, it is possible to incorporate one or more imaging components to enable images of the distal end to be transmitted for display to an operator. The image components may include imaging and light bundle optical fibres that perform the function of a fiberscope, i.e. allowing visual imagery to be coupled from the distal end of the device to the proximal end for connection to a processing unit via a communication cable.

In an embodiment, a fibrescope-based vision system may be realised by forming an optical fibre bundle and an image fibre bundle along the length of the instrument. A lens may be provided at the distal end of the fibre bundle to focus the light and image appropriately. The fibre bundle may be metallized on its outer diameter whereby it can also provide the function of the inner conductor of a coaxial based structure. Alternatively the fibre bundle can be placed alongside the coaxial cable within a protective outer sheath. A third construction method could be to incorporate the fibre bundle into the wall thickness of the outer sheath.

In another embodiment a vision system can be realised using an image sensor (e.g. a suitable CCD/CMOS device) mounted at the distal end of the device, with a communication cable running along the length of the device. A separate illumination fibre bundle or light sources (e.g. LEDs) in the distal end of the device can illuminate the target in order for the image sensor to capture an image. In this embodiment the communication cable may run within or be integrally formed with the inner conductor of the coaxial cable. Alternatively, it may run externally adjacent to the coaxial cable or within the wall thickness of the outer sheath.

Alternatively or additionally, the imaging components may include an ultrasound transducer for ultrasound imagery, and/or a laser light input for spectroscopic imaging.

As discussed above, it is desirable for the instrument to be flexible in order to facilitate movement or rotation at the distal end during treatment. Movement or rotation can be achieved in any suitable manner. For example, one or more guide wires may be provided. Each guide wire may run longitudinally along the instrument and may be pulled at the proximal end in order to cause the distal end to move to one side. In an alternative embodiment, the outer sheath of the instrument may provide a guiding function. For example, one or more guide wires may be extruded into the wall of the outer sheath to allow for control of position of the distal end of the device.

The outer sheath may have a multi-layer or multi-component construction. As explained above, it may carry the coaxial cable, separate control wire(s), a fibre bundle (if provided separately, a communication cable for an image sensor (if provided), wires for a temperature sensor (if provided), etc. The outer sheath may comprise a multi-lumen catheter having a plurality of lumens for conveying these components independently. The outer sheath may be arranged to convey fluid e.g. to cool the coaxial cable and radiating tip. There may be a inflow lumen and outflow lumen to permit circulation of cooling fluid.

Figure 11:
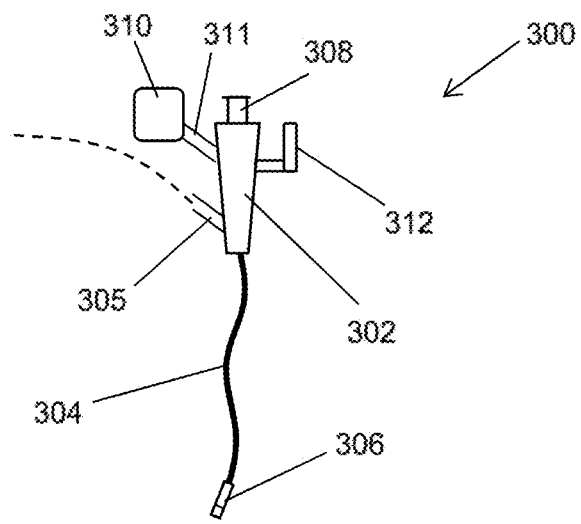
FIG. 11 is a schematic view of a bronchoscope with integrated power delivery that is an embodiment of the invention.

FIG. 11 is a schematic view of a bronchoscope 300 that is another embodiment of the invention. In this embodiment, the coaxial cable discussed above does not travel through the instrument channel of the scoping device. Instead, as discussed in more detail below, a coaxial transmission line structure is integrally formed in the instrument cord of the bronchoscope, e.g. around the instrument channel lumen.

The bronchoscope 300 illustrated in FIG. 11 comprises a body 302 having a number of input ports and an output port from which an instrument cord 304 extends. The instrument cord 304 comprises an outer jacket which surrounds a plurality of lumens. The plurality of lumens convey various things from the body 302 to a distal end of the instrument cord 304. One of the plurality of lumens is the instrument channel discussed above. Other lumens may include a channel for conveying optical radiation, e.g. to provide illumination at the distal end or to gather images from the distal end. The body 302 may include a eye piece 308 for viewing the distal end. In order to provide illumination at the distal end, a light source 310 (e.g. LED or the like) may be connected to the body 302 by an illumination input port 311.

At the distal end of the instrument cord 304 a radiator 306 is mounted. The radiator 306 is arranged to receive microwave energy from a coaxial transmission line structure formed within the instrument cord 304 and emit a microwave field to ablate tissue present at the distal end. The radiator 306 can have a structure corresponding to any of the instruments discussed above with reference to FIGS. 2, 3, 4, 8A-8C, 9A-9B, and 10A-10C.

The body 302 includes a power input port 305 for connecting to a coaxial cable (e.g. a conventional coaxial cable) to transfer microwave energy from a suitable microwave generator (not shown) to the coaxial transmission line structure in the instrument cord 304.

As discussed above, it is desirable to be able to control the position of at least the distal end of the instrument cord 304. The body 302 may include a control actuator 312 that is mechanically coupled to the distal end of the instrument cord 304 by one or more control wires (not shown), which extend through the instrument cord 304. The control wires may travel within the instrument channel or within their own dedicated channels. The control actuator 312 may be a lever or rotatable knob.

Figure 12:
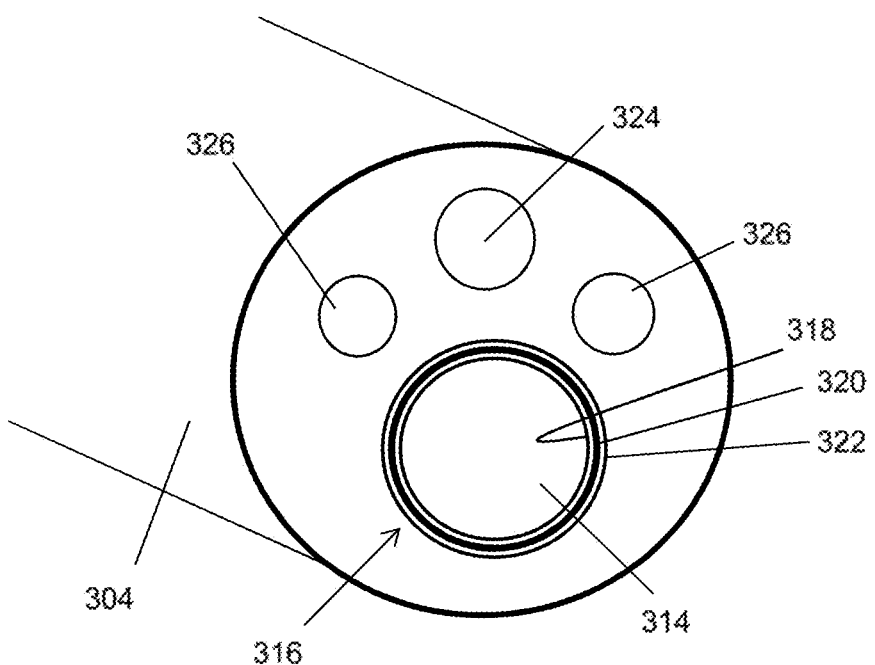
FIG. 12 is a schematic view along the axis of the instrument cord of the bronchoscope shown in FIG. 11.

FIG. 12 is a view down the axis of the instrument cord 304 to show how the coaxial transmission line structure is integrally formed.

In this embodiment there are four lumens within the instrument cord 304. The largest lumen is the instrument channel 314. In this embodiment, a coaxial transmission line structure 316 is formed in the wall of the instrument channel 314. The coaxial transmission line structure 316 comprises an inner conductive layer 318 that is separated from an outer conductive layer 320 by a layer of dielectric material 322. The thicknesses and materials for these layers are selected as known in the art to ensure that the coaxial transmission line structure 316 can convey microwave energy at relatively low loss. There may be a protective layer formed on the inner surface of the inner conductive layer 318.

The other lumens comprise a camera channel 324 and a pair of illumination channels 326, but the invention is not limited to this configuration. For example, there may be other lumens, e.g. for control wires or fluid delivery or suction.

Integrating the means for delivering microwave power into the instrument cord can provide a number of advantages. Firstly, it can enable larger diameter coaxial transmission line structures to be used within a given instrument cord diameter. This may enable the loss of the coaxial transmission line structure to be reduced, which in turn can enable higher power levels to be available at the distal end and/or less heating of the instrument cord during treatment. Secondly, it can free up the instrument channel for other uses. This may mean that the number of lumens and therefore the overall diameter of the instrument cord can be reduced. For example, the instrument channel may be arranged to convey fluid, e.g. for delivery into tissue at the distal end or for cooling the instrument cord during treatment.

Figure 13:
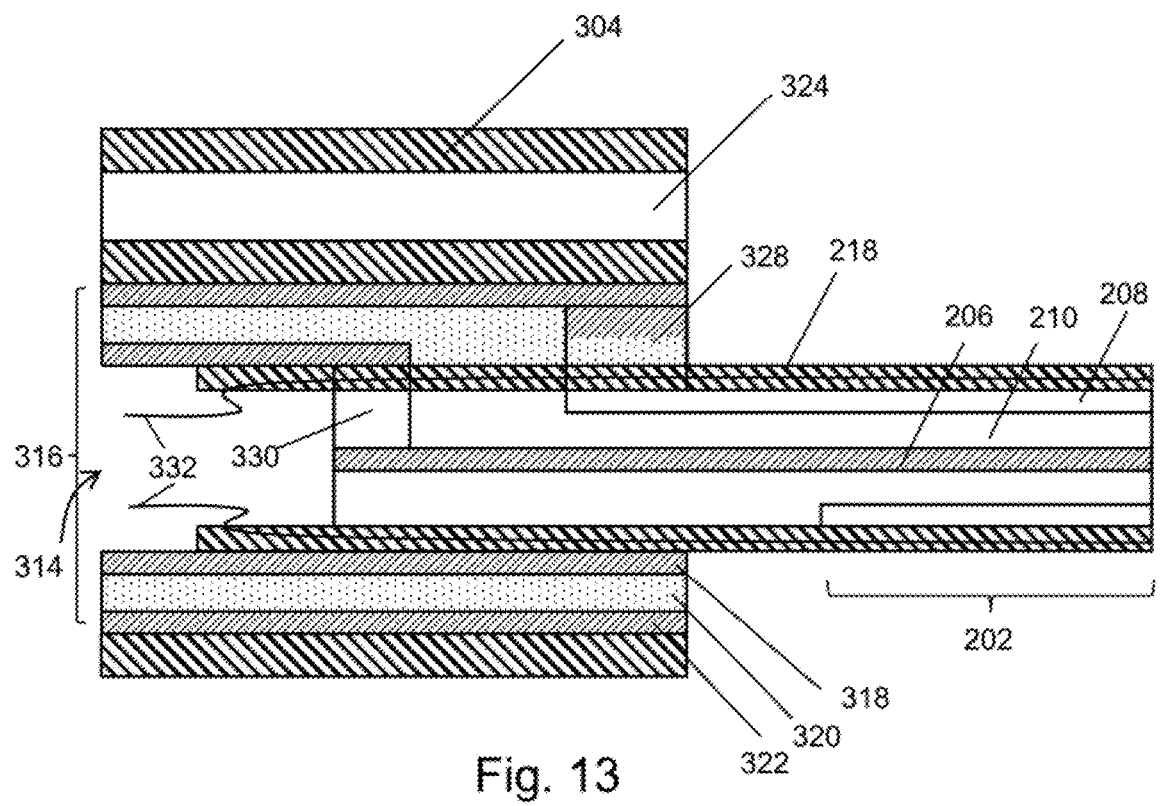
FIG. 13 is a schematic cross-sectional through a distal portion of the instrument cord of a bronchoscope that is a first variant of the embodiment shown in FIG. 11.

FIG. 13 is a schematic cross-section view of a distal end of the instrument cord 304 described above, which show one example of a connection to a radiator. In this example, the radiator comprises a coaxial cable 202 as discussed above. The same reference numbers are used for corresponding features, which are therefore not described again. In FIG. 13 only the proximal end of the coaxial cable 202 is shown. The distal end (not shown) can comprises a radiating tip 204 having the same form as those discussed above.

As shown in FIG. 13, the outer conductor 322 of the coaxial transmission line structure 316 is electrically connected to the outer conductor 208 of the coaxial cable 202 by a first radial conductive element 328, and the inner conductor 318 of the coaxial transmission line structure 316 is electrically connected to the inner conductor 206 of the coaxial cable 202 by a second radial conductive element 330.

A pair of control wires 332 extend through the instrument channel 314 from the control actuator on the body, and are mounted within the outer sheath 218 of the coaxial cable 202. As the coaxial cable is fixed to the distal end of the instrument cord 304, relative longitudinal movement of the control wires 332 within the instrument channel 314 can cause the distal end of the coaxial cable 202 to move from side to side.

The embodiment shown in FIG. 13 shows how a control mechanism (i.e. a steering mechanism) for the radiator can be combined with an integrally formed power delivery configuration. In addition, this embodiment is an example where the power delivery structure is formed from a pair of coaxial transmission lines connected in series, where the outer diameter of the distal coaxial transmission line is less than the outer diameter of the proximal coaxial transmission line. Such a structure can provide and advantageous balance between the problem of power loss and the desire to have a physically small instrument to navigate the bronchial tree. The larger diameter proximal coaxial transmission line may be less lossy than the smaller diameter distal coaxial transmission line, so using this structure can enable power to be more efficiently delivered to a small instrument than would be the case if the same sized coaxial cable were used for the whole length of the instrument cord.

In the example shown in FIG. 13, the instrument channel 314 may be used to circulate fluid, e.g. for the purpose of cooling the coaxial transmission line 316 during treatment.

The distal coaxial cable 202 may be detachable from the instrument cord 304. The structure shown in FIG. 12 may thus be usable with a variety of distal instrument configurations. Some examples are described below with reference to FIGS. 14 to 18. Features in common with FIG. 13 are given the same reference numbers and are not described again.

Figure 14:
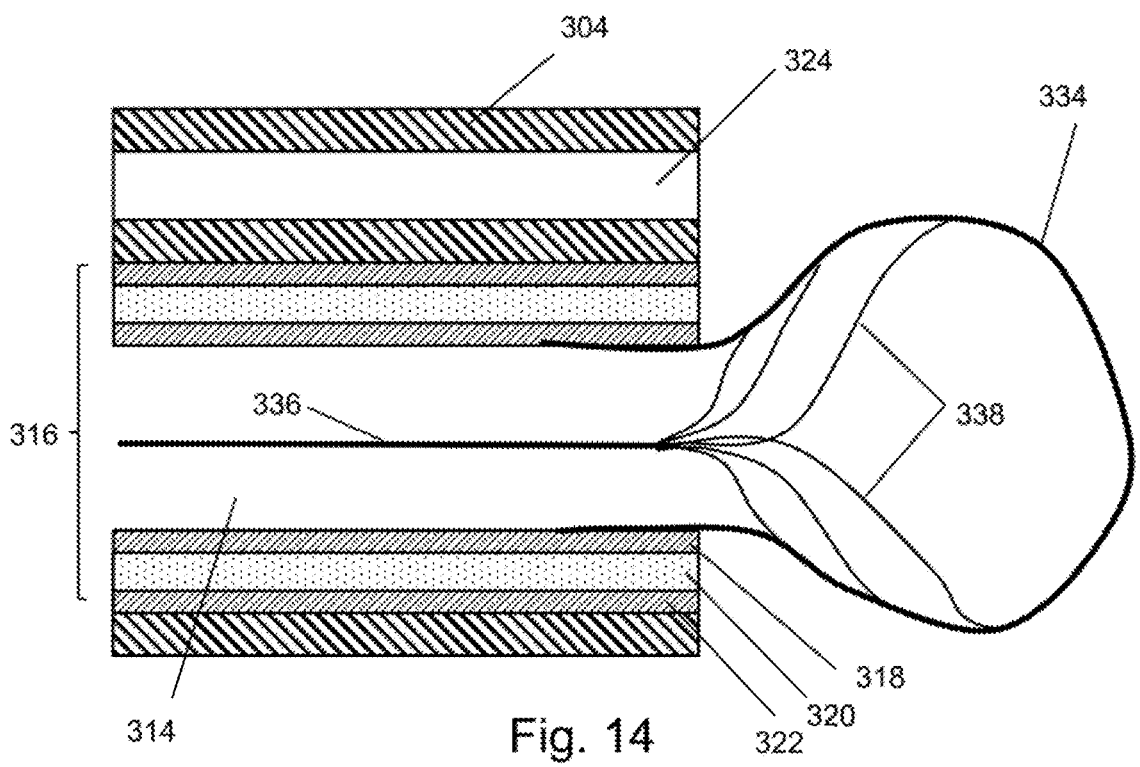
FIG. 14 is a schematic cross-sectional through a distal portion of the instrument cord of a bronchoscope that is a second variant of the embodiment shown in FIG. 11.

FIG. 14 shows an example in which an expandable balloon 334 is mounted at the distal end of the instrument channel. The balloon 334 may be inflated by the application of a suitable fluid through the instrument channel 314, or may be manually operated using a control rod 336, which can be connected to the inner surface of the balloon 334 by a plurality of connecting strands 338. In one example, the balloon 334 may expand using fluid and may be retracted by pulling back on the control rod 336.

The balloon 334 may be made from a flexible dielectric material which can act as a substrate for one or more radiating elements (not shown). The balloon may resemble an aortic balloon. The radiating elements may be patch antennas or the like, which are in electrical communication with the coaxial transmission line structure 316.

Figure 15:
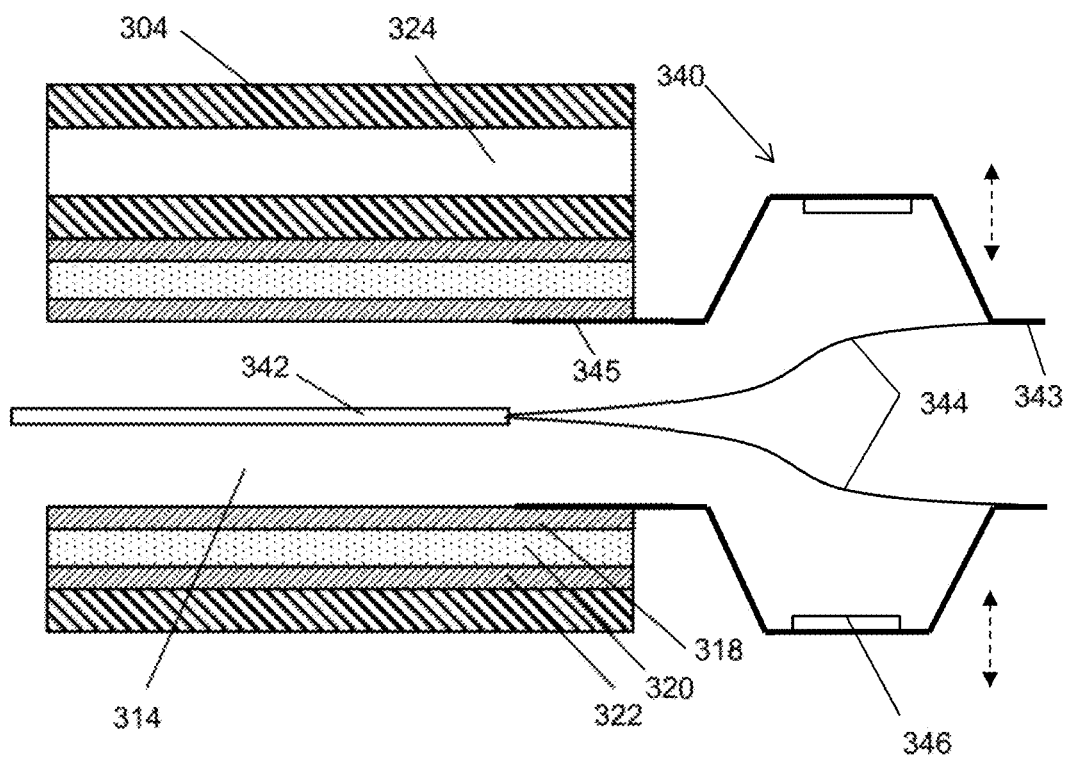
FIG. 15 is a schematic cross-sectional through a distal portion of the instrument cord of a bronchoscope that is a third variant of the embodiment shown in FIG. 11.

FIG. 15 shows an example in which a radially expandable radiating structure 340 is mounted at the distal end of the instrument channel 314. The radiating structure 340 may be tubular with a series of longitudinal slits in its outer surface. When a movable distal end 343 of the radiating structure 340 is brought towards a fixed proximal end 345, the parts of the structure between the slits flares out radially. One or more radiating elements 346, e.g. patch antennas or the like, may be mounted on the parts which flare out. The radiating elements are in electrical communication with the coaxial transmission line structure.

The movable distal end 343 may be connected to a control rod 342 that is mounted in the instrument channel, e.g. via a pair of connector strands 344.

Figure 16:
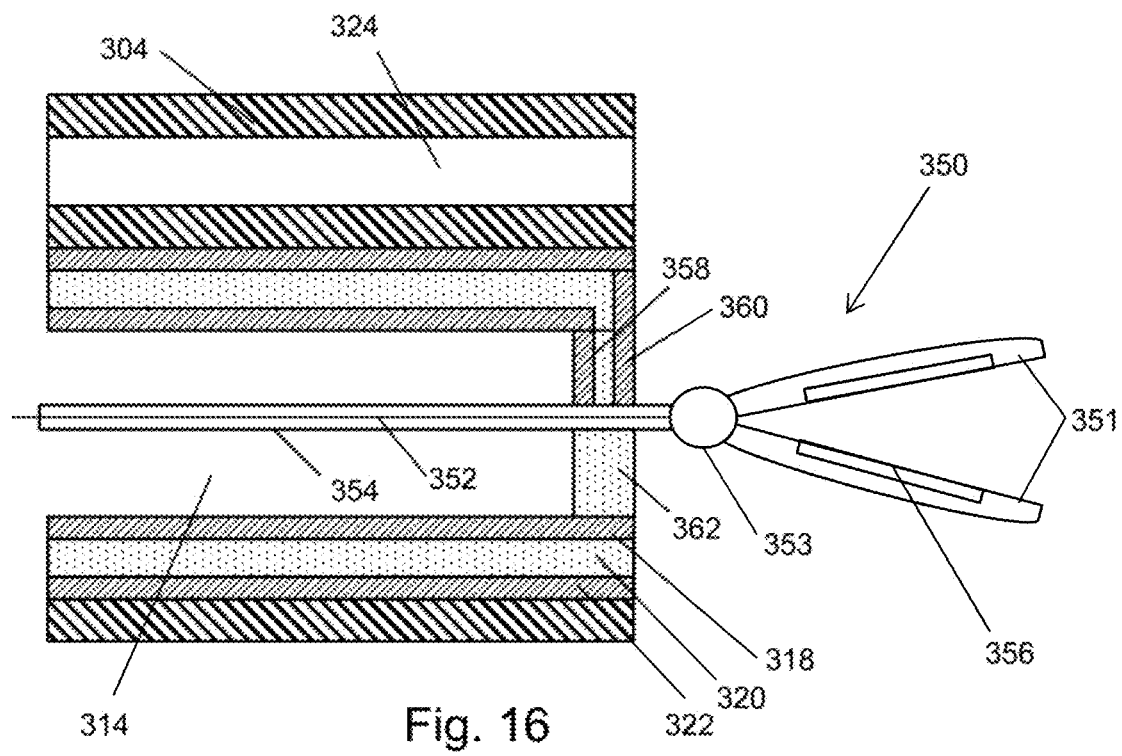
FIG. 16 is a schematic cross-sectional through a distal portion of the instrument cord of a bronchoscope that is a fourth variant of the embodiment shown in FIG. 11.

FIG. 16 shows an example in which a forceps structure 350 is attached at the distal end of the instrument channel 314. The forceps structure 350 comprises a pair of jaws 351 connected at a pivot point 353. The pair of jaws 351 are capable of being opened and closed under operation of a control rod 352, which may be mounted in a fixed sleeve 354 that extends through the instrument channel 314.

One or both of the pair of jaws 351 has a radiating element 356 (e.g. patch antenna or the like) formed thereon, e.g. at an inner surface thereof. The radiating element 356 is in electrical communication with the coaxial transmission line structure 316. In this example, the forceps structure 350 may be secured in the instrument channel 314 by a distal cap 362. The distal cap 362 may include a paid of radial conductive elements 358, 360 for providing electrical connections between the radiating element 351 and the inner conductor 318 and outer conductor 322 respectively of the coaxial transmission line structure 316.

The forceps structure 350 can be used to grasp tissue in the bronchial tree.

Figure 17:
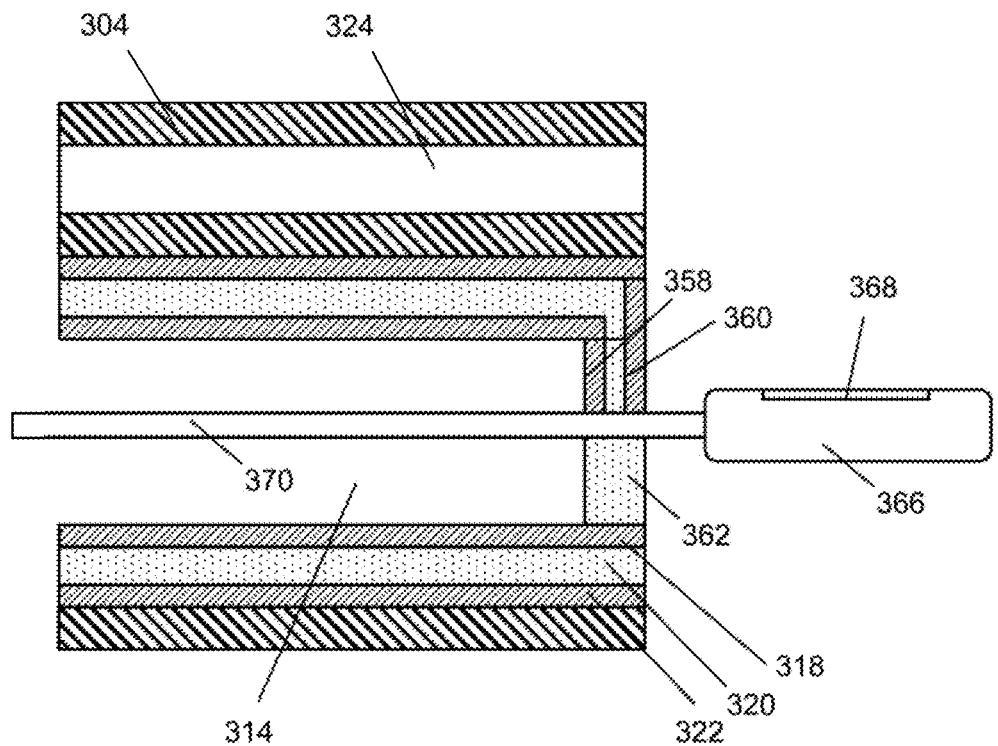
FIG. 17 is a schematic cross-sectional through a distal portion of the instrument cord of a bronchoscope that is a fifth variant of the embodiment shown in FIG. 11.

FIG. 17 shows an example in which a paddle structure 364 is attached at the distal end of the instrument channel. Feature in common with FIG. 16 are given the same reference number and are not described again. The paddle structure 364 comprises a dielectric body 366 with one or more radiating elements 368 (e.g. patch antennas or the like) fabricated thereon. The radiating elements are electrically connected to the coaxial transmission line structure, e.g. via the radial conductive elements 358, 360. The position of the paddle may be controlled using a control rod 370.

Figure 18:
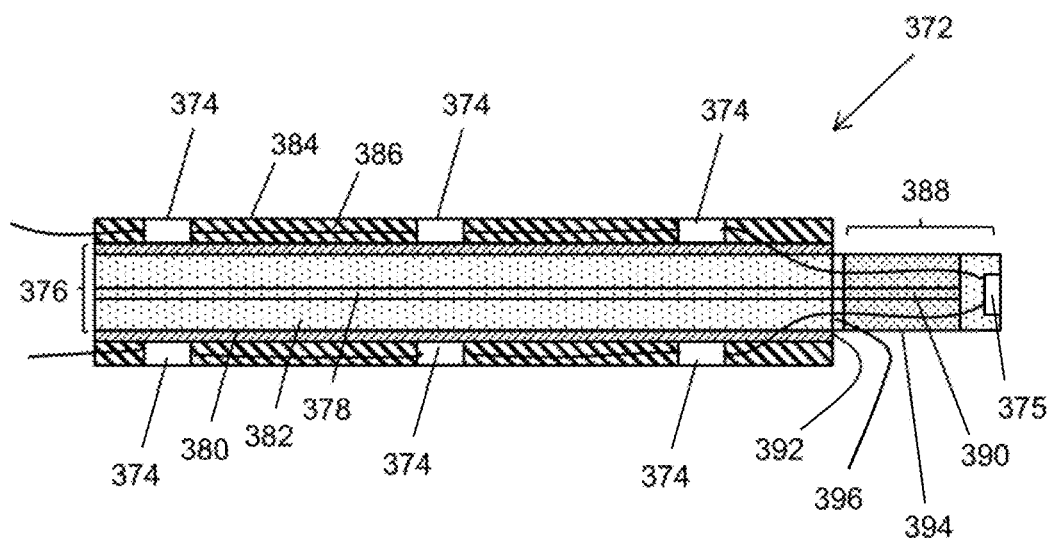
FIG. 18 is a schematic cross-sectional through a distal radiator that can be used with the embodiment shown in FIG. 11.

FIG. 18 shows a schematic distal tip portion 372 that incorporates temperature sensors 374 (e.g. thermocouples). The distal tip portion comprises a coaxial cable that can extend through the instrument channel of a bronchoscope or which can be connected at the distal end of a hollow coaxial transmission line structure that is integrated within the instrument cord, as discussed above.

In detail, the top portion 372 comprises a coaxial cable 376 comprising an inner conductor 378 separated from an outer conductor 380 by a first dielectric material 382. The coaxial cable may be the same as the coaxial cable 202 discussed above. The coaxial cable 376 is encased in a outer jacket 384, which have a plurality of temperature sensors 374 mounted therein. Signal lines 386 for the temperature sensors are also carried in the outer jacket 384. The signal lines 386 extend proximally out of the instrument to provide information from the temperature sensors to an external monitoring device (not shown).

At the distal end of the coaxial cable 376 there is a radiating tip section 388 that comprises a distal conductive section 390 of the inner conductor 378 that extends beyond a distal end 392 of the outer conductor 380. The distal conductive section 390 is surrounded at is distal end by a dielectric tip 394 formed from a second dielectric material, which is different from the first dielectric material 382. The length of the dielectric tip 394 is shorter than the length of the distal conductive section 390. An intermediate dielectric sleeve 396 surrounds the distal conductive section 390 between the distal end of the coaxial cable 376 and the proximal end of the dielectric tip 394. The intermediate dielectric sleeve 396 is formed from a third dielectric material, which is different from the second dielectric material but which may be the same as the first dielectric material 382.

The radiating tip section 388 acts in the same manner as described above with respect to FIG. 3 in that it reduces the wavelength of the microwave energy to provide a more focussed field. Indeed, the radiating tip section may be configured in the same way as shown in any of FIGS. 2, 3, 4, 8A-8C, 9A-9B, and 10A-10C.

A dielectric cap 398 formed of a fourth dielectric material, which is different from the second dielectric material but may be the same as the first or third dielectric material 382, 396 is formed at the distal end of the dielectric tip 394. Similarly to FIG. 3, the second dielectric material may be $TiO_2$ and the third dielectric material may be PFTE. The fourth dielectric material may also be PTFE. A temperature sensor 375 can be mounted in the dielectric cap 398. Signal lines from the temperature sensor 375 in the dielectric cap 398 may pass through the dielectric tip 394.

As the signal lines for the temperature sensors are so close to the transmission line that carries the microwave energy, it may be necessary to take action to avoid the microwave energy swamping a response signal from the temperature sensors. In one example, this can be done by delivering the microwave energy in a series of pulses and taking readings from the temperature sensors in the gaps between the pulses.

Figure 19:
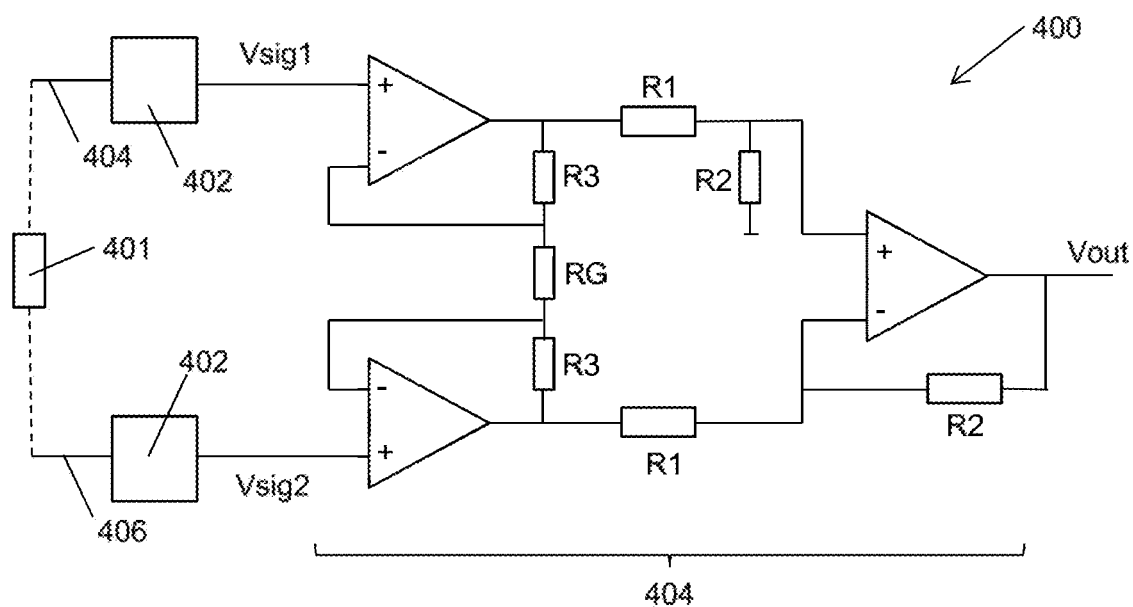
FIG. 19 is a schematic circuit diagram for an instrumentation amplifier that can be used with the distal radiator of FIG. 18.

In another example, the response signals from the temperature sensors may be extracted by filtering out any noise due to the microwave energy. FIG. 19 shows an example of a suitable filtering arrangement 400 for a thermocouple 401. The filter arrangement 400 comprises a pair of low pass filters 402 and an instrumentation amplifier 404 arranged to remove any common noise from signals $V_{sig1}$, $V_{sig2}$ on the wire legs 404, 406 of the thermocouple 401.

In the arrangement shown in FIG. 19, the output signal $V_{out}$ can be expressed as $$V_{out} = (V_{sig1} - V_{sig2})\frac{R_2}{R_1}\left(1 + \frac{2R_3}{R_G}\right)$$

Figure 20:
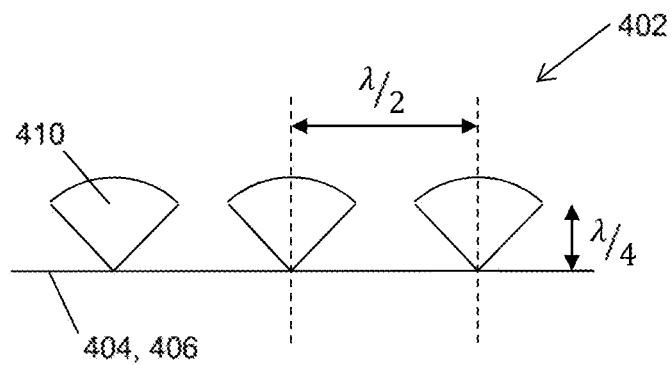
FIG. 20 is a schematic diagram of a low pass filter that that can be used with the distal radiator of FIG. 18.

FIG. 20 shows an example of a suitable low pass filter 402 for the filtering arrangement 400. The low pass filter 402 comprises a plurality (preferably three) stubs 410 formed on each wire leg 404, 406 of the thermocouple. The stubs 410 are separated by a multiple of a half wavelength of the microwave energy, and have a height equal to an odd multiple of a quarter wavelength of the microwave energy.

The invention claimed is:

1. An electrosurgical instrument for delivering microwave energy into biological tissue, the electrosurgical instrument comprising:
   a coaxial cable for conveying the microwave energy, the coaxial cable having an inner conductor, an outer conductor, and a first dielectric material separating the inner conductor and outer conductor;
   a radiating tip portion disposed at a distal end of the coaxial cable to receive the microwave energy from the coaxial cable; and
   an imaging element for conveying an imaging signal to permit visualisation of a distal end of the instrument, wherein the radiating tip portion comprises:
   a dielectric tip formed from a second dielectric material that is different from the first dielectric material, and a distal conductive portion comprising a portion of the inner conductor of the coaxial cable as a singular element that extends longitudinally into the dielectric tip and is surrounded by the dielectric tip, wherein the second dielectric material has a dielectric constant greater than the first dielectric material, a geometry of the second dielectric material and its dielectric constant being selected such that an axial length of the dielectric tip corresponds to a fraction of a wavelength of the microwave energy when propagating in the dielectric tip, whereby the radiating tip portion is arranged as a quarter wave impedance transformer to match an input impedance to a tissue load impedance to radiate a localized microwave field for tissue ablation, wherein the imaging element extends through the first dielectric material and radiating tip portion within the inner conductor, the distal conductive portion, and the dielectric tip, wherein the distal conductive portion extends longitudinally through the dielectric tip and terminates at a proximal end of a dielectric cap, wherein the distal conductive portion abuts the proximal end of the dielectric cap.

2. The electrosurgical instrument according to claim 1, wherein an outer diameter of the coaxial cable and radiating tip portion is equal to or less than 1.9 mm.

3. The electrosurgical instrument according to claim 1, wherein the dielectric constant of the second dielectric material is equal to or greater than 80.

4. The electrosurgical instrument according to claim 1, wherein the radiating tip portion further comprises an intermediate dielectric element surrounding a proximal part of the distal conductive portion and separating the first dielectric material from the dielectric tip, the intermediate dielectric element being formed from a third dielectric material that is different from the second dielectric material.

5. The electrosurgical instrument according to claim 1, comprising conductive material arranged on an outer surface of the dielectric tip to form a microstrip or coplanar transmission line for delivering the microwave energy into the biological tissue.

6. The electrosurgical instrument according to claim 1, wherein the radiating tip portion includes a field shaping element arranged to direct the microwave field to one side of the radiating tip portion.

7. The electrosurgical instrument according to claim 6, wherein the field shaping element is a conductive finger extending longitudinally along a side of an outer surface of the dielectric tip opposite to the side from which the microwave field is directed, the conductive finger being electrically connected to the outer conductor of the coaxial cable.

8. The electrosurgical instrument according to claim 7, wherein the conductive finger extends along an outer surface of the dielectric cap, whereby the conductive finger extends further from the coaxial cable than the distal conductive portion.

9. The electrosurgical instrument according to claim 7, wherein the conductive finger is an extension of the outer conductor of the coaxial cable.

10. The electrosurgical instrument according to claim 7, wherein the conductive finger is a distal part of a conductive sleeve mounted on and electrically connected to the outer conductor of the coaxial cable, wherein the conductive sleeve is rotatable relative the dielectric tip to adjust a circumferential position of the conductive finger.

11. The electrosurgical instrument according to claim 6, wherein the field shaping element is a conductive sleeve formed over the dielectric tip, the conductive sleeve having a radiating slot formed therein on the side from which the microwave field is directed.

12. The electrosurgical instrument according to claim 11, wherein the conductive sleeve is rotatable relative the dielectric tip to adjust a circumferential position of the radiating slot.

13. The electrosurgical instrument according to claim 10, wherein the conductive sleeve has a pair of radiating slots on opposite sides of the dielectric tip, and wherein a radiating top portion comprises an actuator operable to selectively expose only one slot of the pair of radiating slots.

14. The electrosurgical instrument according to claim 13, where in the actuator comprises a longitudinally slidable sleeve having opposed cut outs formed therein, wherein the actuator is movable between a first position in which a first cut out of the opposed cut outs exposes a first one of the pair of radiating slots and a second position in which a second cut out of the opposed cut outs exposes a second one of the pair of radiating slots.

15. The electrosurgical instrument according to claim 1, wherein the imaging element includes a fibrescope comprising a bundle of optical fibres.

16. The electrosurgical instrument according to claim 15, wherein the inner conductor and distal conductive portion are hollow to define a channel for carrying the bundle of optical fibres.

17. The electrosurgical instrument according to claim 15, wherein the bundle of optical fibres extends through the first dielectric material and the radiating tip portion and has a layer of conductive material over its outer surface to form the inner conductor of the coaxial cable and the distal conductive portion.

18. The electrosurgical instrument according to claim 1, wherein the imaging element comprises an image sensor mounted at the distal end of the radiating tip portion and a communication cable for conveying a signal from the image sensor to a proximal end of the instrument.

19. The electrosurgical instrument according to claim 18, wherein the inner conductor and the distal conductive portion are hollow to define a channel for carrying the communication cable.

20. The electrosurgical instrument according to claim 18, wherein the image sensor comprises an ultrasound transducer.

21. The electrosurgical instrument according to claim 1 including a temperature sensor at the distal end thereof.

22. The electrosurgical instrument according to claim 21, wherein the temperature sensor is a thermocouple mounted on the outer conductor of the coaxial cable.

23. The electrosurgical instrument according to claim 22, wherein the thermocouple comprises a plurality of stubs arranged to filter out a signal having a same frequency as the microwave energy.

24. The electrosurgical instrument according to claim 21, wherein the temperature sensor includes a temperature sensitive micromechanical structure at the distal end of the end, and a means of optically monitoring the temperature sensitive micromechanical structure.

25. The electrosurgical instrument according to claim 1, wherein the coaxial cable is mounted in an outer sheath, and wherein the outer sheath is a multi lumen catheter arranged to convey any one or more of:

guide wires for controlling movement of the radiating tip portion, and fluid for cooling the distal end of the instrument.

26. An electrosurgical apparatus for delivering microwave energy into lung tissue, the electrosurgical apparatus comprising:

a generator for generating the microwave energy;

a bronchoscope for non-percutaneous insertion into a patient's lungs, the bronchoscope having an instrument channel running along its length; and an electrosurgical instrument mounted in the instrument channel of the bronchoscope, the electrosurgical instrument comprising:

a coaxial cable for conveying the microwave energy, the coaxial cable having an inner conductor, an outer conductor, and a first dielectric material separating the inner conductor and outer conductor;

a radiating tip portion disposed at a distal end of the coaxial cable to receive the microwave energy from the coaxial cable; and an imaging element for conveying an imaging signal to permit visualisation of a distal end of the instrument, wherein the radiating tip portion comprises:

a dielectric tip formed from a second dielectric material that is different from the first dielectric material, and a distal conductive portion comprising a portion of the inner conductor of the coaxial cable as a singular element that extends longitudinally into the dielectric tip and is surrounded by the dielectric tip, wherein the second dielectric material has a dielectric constant greater than the first dielectric material, a geometry of the second dielectric material and its dielectric constant being selected such that an axial length of the dielectric tip corresponds to a fraction of a wavelength of the microwave energy when propagating in the dielectric tip, whereby the radiating tip portion is arranged as a quarter wave impedance transformer to match an input impedance to a tissue load impedance to radiate a localized microwave field for tissue ablation;

wherein the imaging element extends through the first dielectric material and radiating tip portion within the inner conductor, distal conductive portion, and the dielectric tip; and wherein the coaxial cable is connected to receive the microwave energy from the generator;

wherein the distal conductive portion extends longitudinally through the dielectric tip to an end of the dielectric tip and terminates at a proximal end of a dielectric cap, wherein the distal conductive portion abuts the proximal end of the dielectric cap.

27. The electrosurgical apparatus according to claim 26, wherein the generator is arranged to deliver pulses of microwave energy in time with a breathing cycle of the patient.

28. The electrosurgical instrument according to claim 6, wherein the field shaping element is arranged along one side of the dielectric tip to direct a majority of the microwave field to an opposite side of the dielectric tip.

* * * * *